(12) United States Patent
Kunz et al.

(10) Patent No.: US 7,892,852 B2
(45) Date of Patent: Feb. 22, 2011

(54) METHOD FOR DETERMINING THE ENDOGENOUS ANTIOXIDATIVE POTENTIAL OF BEVERAGES BY MEANS OF ESR SPECTROSCOPY

(75) Inventors: Thomas Kunz, Trier (DE);
Frank-Jurgen Methner, Bitburg (DE);
Jurgen Huttermann, Homburg (DE);
Reinhard Kappl, Homburg (DE)

(73) Assignee: Technische Universitat Berlin, Berlin (DE)

( * ) Notice: Subject to any disclaimer, the term of this patent is extended or adjusted under 35 U.S.C. 154(b) by 41 days.

(21) Appl. No.: 12/066,160

(22) PCT Filed: Sep. 8, 2006

(86) PCT No.: PCT/EP2006/008784
§ 371 (c)(1),
(2), (4) Date: Apr. 16, 2008

(87) PCT Pub. No.: WO2007/028635
PCT Pub. Date: Mar. 15, 2007

(65) Prior Publication Data
US 2008/0248580 A1 Oct. 9, 2008

(30) Foreign Application Priority Data
Sep. 10, 2005 (DE) .................. 10 2005 043 113

(51) Int. Cl.
*G01N 24/00* (2006.01)
*G01N 33/00* (2006.01)
(52) U.S. Cl. .................. 436/173; 436/243; 436/34; 436/132
(58) Field of Classification Search .......... 436/173; 426/12
See application file for complete search history.

(56) References Cited

U.S. PATENT DOCUMENTS
2009/0041890 A1* 2/2009 Festersen et al. ............. 426/12

FOREIGN PATENT DOCUMENTS
EP 0 720 026 A2 7/1996
WO WO 2005/003759 1/2005

OTHER PUBLICATIONS

Logan et al., 1999, Alcohol Content of Beer and Malt Beverages: Forensic Considerations, Indiana University: Center for Studies of Law in Action Technical Note.*

(Continued)

*Primary Examiner*—Krishnan S Menon
*Assistant Examiner*—Allison Gionta
(74) *Attorney, Agent, or Firm*—Pearl Cohen Zedek Latzer, LLP

(57) ABSTRACT

The present invention relates to a method for determining the endogenous antioxidative potential (EAP) in a beverage sample, preferably beer, wine, juice or mixtures thereof, using ESR spectroscopy. More specifically, the invention relates to a method for measuring a secondary radical, preferably a hydroxyethyl radical, which is stabilized by a spin trap reagent, wherein the spin trap reagent is preferably, N-tert-butyl-α-(4-pyridyl)nitrone N-oxide (POBN). The invention also relates to the use of the method for assessing the oxidative stability of a beverage sample, to the use of a spin trap reagent, preferably POBN, for measuring the EAP, and to a kit for carrying out the method. The invention is characterized in that a method is provided which makes it possible to avoid the pH effect occurring in prior art methods and the associated influence on the generation of radicals in the beverage sample to be measured.

29 Claims, 13 Drawing Sheets

OTHER PUBLICATIONS

Aoshima et al., Generation of Free Radicals during the Death of *Saccharomyces cerevisiae* Caused by Lipid Hydroperoxide, 1999, Biosci. Biotechnol. Biochem., 53(6), 1025-1031.*

Andersen M.L. et al., "Modification of the levels of Polyphenols in Wort and Beer by addition of Hexamethylenetetramine or Sulfite during Mashing", Journal of Agricultural and Food Chemistry, American Chemical Society, No. 49, pp. 5232-5237, Oct. 23, 2001.

Kunz T. et al., "Fundamentals on electron spin resonance spectroscopy (ESR) and research about the correlation between oxidative beer stability and sulphite content", Monatsschrift Fuer Brauwissenschaft 55, No. 7/8, pp. 140-153, 2002. (Translation of Abstract only at p. 152).

Pascual E. C. et al., "Characterization of free radicals in soluble coffee by electron paramagnetic resonance spectroscopy", Journal of Agricultural and Food Chemistry, vol. 50, No. 21, Oct. 9, 2002, pp. 6114-6122.

Kocherginsky N.M. et al., "Antioxidant pool in beer and kinetics of EPR spin-trapping", Journal of Agricultural and Food Chemistry, vol. 53, No. 17, Aug. 24, 2005, pp. 6870-6876.

Andersen M.L. et al., "Potential antioxidants in beer assessed by ESR spin trapping", Journal of Agricultural and Food Chemistry, vol. 48, No. 8, Aug. 2000, pp. 3106-3111.

* cited by examiner

Figure 1
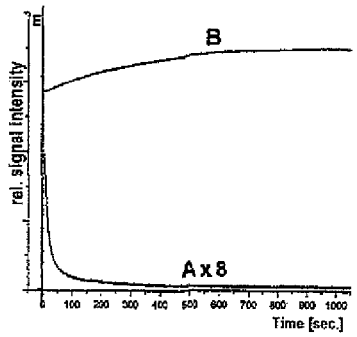
Figure 1A
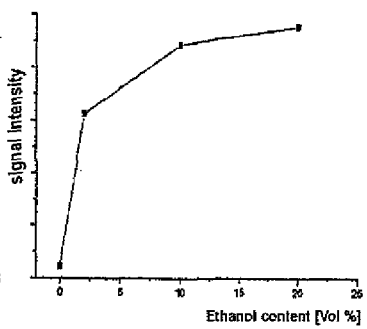
Figure 1B
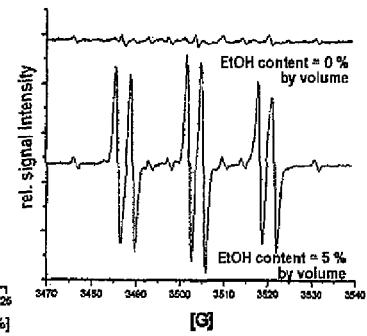
Figure 1C
Figure 2
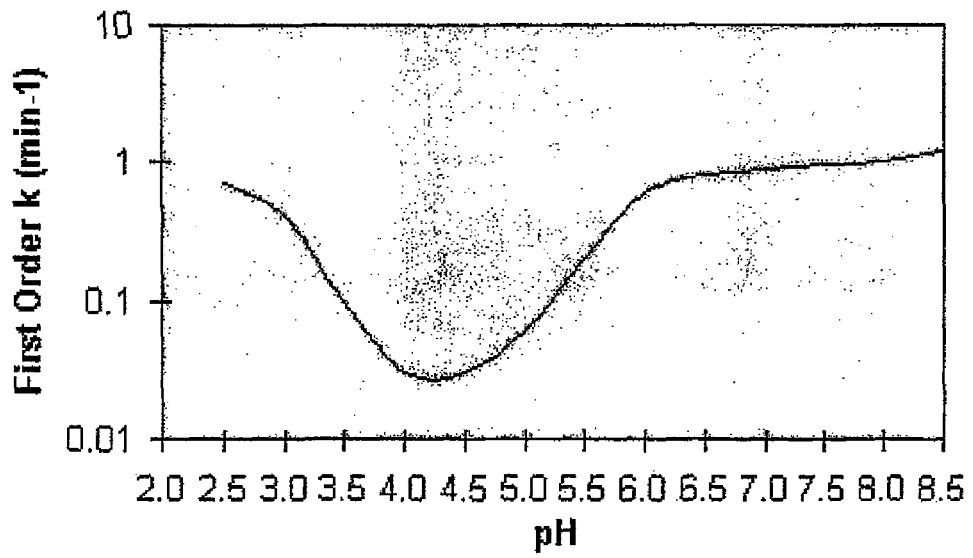

Figure 9
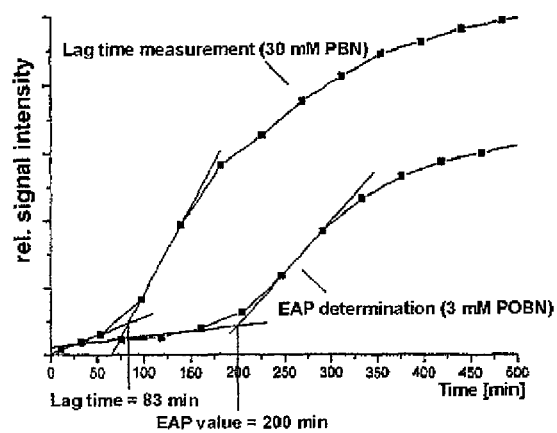
Figure 9A
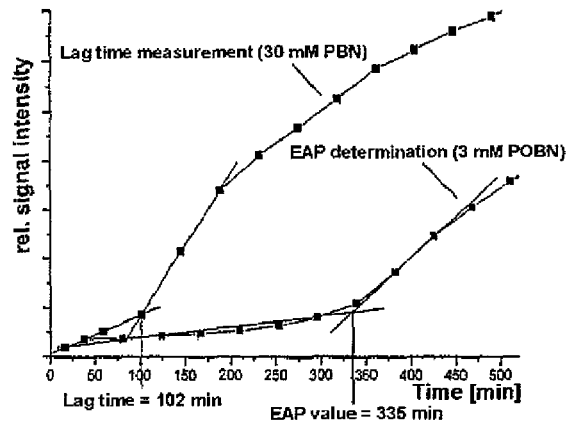
Figure 9B

METHOD FOR DETERMINING THE ENDOGENOUS ANTIOXIDATIVE POTENTIAL OF BEVERAGES BY MEANS OF ESR SPECTROSCOPY

CROSS-REFERENCE TO RELATED APPLICATIONS

This application is a National Phase Application of PCT International Application No. PCT/EP2006/008784, International Filing Date Sep. 8, 2006, which claimed priority from German Patent Application No. 10 2005 043 113.5, filed Sep. 10, 2005, which is hereby incorporated by reference.

The present invention relates to a method for determining the endogenous antioxidative potential (EAP) in a beverage sample, preferably beer, wine, juice or mixtures thereof, using ESR spectroscopy. More specifically, the present invention relates to a method for measuring a secondary radical, preferably a hydroxyethyl radical, which is stabilized by a spin trap reagent, wherein the spin trap reagent is preferably N-tert-butyl-α-(4-pyridyl)nitrone N-oxide (POBN). The invention also relates to the use of the method for assessing the oxidative stability of a beverage sample, to the use of a spin trap reagent, preferably POBN, for measuring the EAP, and to a kit for carrying out the method according to the invention.

BACKGROUND OF THE INVENTION

Appearance and taste are the main criteria used by consumers to assess a beer, but also other beverages such as e.g. wine, juice or mixed beverages. The so-called "flavor", which results from the synergy between the gustatory and olfactory sensations, should therefore remain as constant as possible for the entire duration up until the specified best before date. However, the natural aging process of a beverage, preferably a beer, works against this. For this reason, the flavor stability is becoming increasingly important as an essential quality feature of beer.

The oxidative flavor stability is substantially dependent on the extent to which a beer is able to prevent the formation of primary oxygen radicals ($O^-_2$.; OH.; H.; $HO_2$.) and is accordingly influenced by the endogenous antioxidative potential (EAP) of a beer, which is based on reducing compounds such as e.g. sulfur dioxide ($SO_2$), Maillard reaction products, ascorbic acid and phenolic ingredients.

The radicals produced in the course of beer aging are usually initiated via various forms of activated oxygen, which therefore plays an important role in the onset of the aging flavor. Among the primary oxygen radicals, particular mention should be made of the hydroxyl radical produced via the Fenton and Haber-Weiss reaction; this radial assumes a key position in beer aging. If the production of hydroxyl radicals can be reduced or even prevented, it is possible to delay the onset of the aging flavor, which is brought about in particular by carbonyl compounds, and especially aliphatic aldehydes [5, 6, 14, 15].

Beers are able to prevent the formation of hydroxyl radicals for a certain period of time before the generation of radicals proceeds unhindered. Under identical external conditions (e.g. temperature, oxygen contact, etc.) and with constant conditions in a beer sample (e.g. pH, dissolved oxygen, etc.), the period of time over which the generation of radicals can be prevented or delayed is directly related to the existing EAP.

With the aim of being able to make a statement about the flavor stability that can be expected of a beer, for some years use has been made of electron spin resonance (ESR) spectroscopy. In this process, the so-called "lag time" of a beer is determined via an experimentally accelerated ("forced") beer aging at increased temperatures ("forcing test", usually at 60° C.). The lag time value corresponds to the point in time from which the generation of radicals in the beer proceeds unhindered under defined experimental conditions, and the value of the lag time determined using this measurement method is considered to be a criterion for the EAP of the beer [1-11].

In this measurement method, which was first described by Kaneda et al. [12] and was further developed by Uchida et al. [1], the property of ESR spectroscopy is used to selectively detect radicals with a high level of sensitivity in the complex system comprising beer with a large number of different ingredients. Since radicals in aqueous solutions usually have only a very short life span, it is necessary to use a radical scavenger ("spin trap") which is able to accumulate diffusible radicals. With the spin trap reagent N-tert-butyl-α-phenylnitrone (PBN) selected by Uchida et al. [1], a much more stable nitroxide radical is produced which accumulates to a sufficient extent over time and can thus be detected by ESR spectroscopy on the basis of its spectral characteristic [13].

The mechanism of lag time measurement according to the known method has been interpreted so that it is the hydroxyl radicals which are important with regard to oxidative beer aging, and the time-dependent formation of said radicals is detected using the spin trap reagent PBN during the forcing test.

Besides ESR spectrometers in research equipment, the company Bruker (Karlsruhe) offers a table-top device called "e-scan" (small X-band ESR spectrometer), by means of which the lag time can be determined using the method described above in the laboratories of the beverage-producing industry.

However, the described method exhibits significant weaknesses and falsifications. In this connection, reference is made in particular to a pH effect which is brought about by the spin trap reagent PBN that is used. This effect leads to the pH of a beer sample rising during the lag time measurement as a function of the PBN concentration used. According to Bishop et al. [19] and Millero et al. [20], a rise in the pH, in particular in the pH range >4.5 (Fenton reaction), leads to excessive acceleration of the generation of hydroxyl radicals.

The rise in pH dependent on the PBN concentration (pH effect) during the lag time measurement accelerates the generation of radicals in the beer, and the existing EAP is used up increasingly quickly over the duration of the lag time measurement. The point in time at which unhindered radical generation starts (measured lag time) deviates to a correspondingly large extent from the conditions that actually exist in the beer. Even for this reason alone, the lag time measurement according to the previous method is not readily suitable for correctly determining the EAP of a beer.

To complicate matters, added to this is the fact that the degree of falsification caused by the addition of PBN with regard to the time of unhindered radical generation (pH effect) is additionally influenced by the existing EAP of a beer. This can be explained by the fact that the pH effect on the generation of radicals within the lag time is different for beers with different EAPs. As a result, the generation of radicals within a high lag time is influenced for a greater length of time and to a greater extent—since higher pH values are achieved—towards an increased generation of hydroxyl radicals, and the difference between the measured lag time and the conditions that actually exist in the beer increases accordingly.

Another falsification factor is the fact that many ingredients with an antioxidative effect (e.g. phenolic substances, etc.) are pH-dependent with regard to their action. Since there are many falsifications and the differences in the case of beers with a medium to high oxidative beer stability are up to 600%, for many or most beers it is no longer possible to establish any connection to the EAP. The lag time measurement according to the previous procedure is unsuitable for determining the EAP of the beers, and the results obtained have recently led to corresponding misinterpretations in various publications. Not only are the effects of the beer ingredients on the oxidative beer stability greatly falsified, but also the brewing measures based on these measurements to improve the oxidative beer stability are falsely estimated on the basis of the results.

In the prior art [16, 17], there are also indications that the radicals detected with PBN are in the main not hydroxyl radicals themselves but rather that the hydroxyethyl radicals produced as the result of a subsequent reaction of the hydroxyl radical with the ethanol of the beer are involved to a greater extent than the previously assumed few percent in the measured signal intensity. The reason given for this was a higher stability of the stabilized hydroxyethyl PBN spin adducts [17]. The question as to which radicals ultimately play a role in the lag time determination is particularly important not just with regard to the method itself, but may also be particularly useful for the further clarification of the aging processes, which are not yet fully known.

There is therefore a need for an improved method for assessing the flavor stability of beer and other oxidative beverages.

It was therefore an object of the present invention to provide a method which can be used to determine the EAP of beer and other beverages in a more reliable manner than before.

SUMMARY OF THE INVENTION

The object of the present invention is achieved by a method for determining an EAP in a sample, comprising the qualitative and/or quantitative analysis of a secondary radical, which is stabilized by a spin trap reagent, using ESR spectroscopy, wherein the spin trap reagent is suitable for making it possible to avoid the pH effect and the associated influence on the generation of radicals in the sample.

In one embodiment, the sample is a beverage sample selected from the group consisting of a sample of beer, wine, juice and mixtures thereof.

In one preferred embodiment, the sample is a beer sample.

In one embodiment, the spin trap reagent is POBN.

In one preferred embodiment, the concentration of the spin trap reagent in the sample is approximately $\leq 10$ mM.

In one particularly preferred embodiment, the concentration of the spin trap reagent in the sample is approximately 3 mM.

In one embodiment, the spin trap reagent is soluble in the sample and preferably is dissolved in the sample.

In an alternative embodiment, the spin trap reagent is dissolved in an aqueous ethanol solution or another aqueous solution before being added to the sample.

In one embodiment, the secondary radical is a hydroxyethyl radical.

In one embodiment, the method comprises the following steps:
(a) providing the sample;
(b) adding the spin trap reagent;
(c) carrying out the analysis;
(d) determining the EAP value.

In one preferred embodiment, the carrying-out of the analysis in step (c) comprises carrying out a forcing test.

In one particularly preferred embodiment, the forcing test is carried out at a temperature in the range from approximately $\geq 40°$ C. to approximately $\leq 96°$ C.

In a further particularly preferred embodiment, the forcing test is carried out at a temperature in the range from approximately $\geq 60°$ C. to approximately $\leq 96°$ C.

In a further particularly preferred embodiment, the forcing test is carried out at a temperature in the range from approximately 63-65° C. with beer as the sample, approximately 65-70° C. with wine as the sample, and approximately 60° C. with juice as the sample.

In a further particularly preferred embodiment, the forcing test is carried out at a temperature of approximately 63° C.

In one preferred embodiment, the forcing test is carried out at a pH which lies in a range extending from approximately one pH point below to approximately one pH point above the pH of the sample.

In a further particularly preferred embodiment, the forcing test is carried out at a pH which lies in a range extending from approximately 0.5 pH point below to approximately 0.5 pH point above the pH of the sample.

In a further particularly preferred embodiment, the forcing test is carried out at a pH which corresponds approximately to the pH of the sample.

In a further particularly preferred embodiment, the forcing test is carried out in the presence of ethanol in the range from approximately 0.01-20% by volume.

In a further particularly preferred embodiment, the forcing test is carried out in the presence of ethanol in the range from approximately 0.01-10% by volume.

In a further particularly preferred embodiment, the forcing test is carried out in the presence of ethanol in the range from approximately 0.01-6.0% by volume.

In a further particularly preferred embodiment, the forcing test is carried out in the presence of ethanol in the range from 0.01-3.0% by volume.

In one preferred embodiment, the carrying-out of the analysis in step (c) comprises the following sub-steps:
(c1) taking a measurement sample at a given time;
(c2) recording the ESR spectrum of the measurement sample.

In one particularly preferred embodiment, the time period between sub-steps (c1) and (c2) is approximately $\leq 15$ min.

In a further particularly preferred embodiment, the time period between sub-steps (c1) and (c2) is approximately 4 min.

In one embodiment, the method comprises a system which promotes the generation of radicals.

In one embodiment, the method comprises the qualitative and/or quantitative analysis of the effect of an oxidatively neutral, antioxidative or oxidative compound selected from the group consisting of oxygen, $SO_2$, Maillard reaction products, ascorbic acid (vitamin C) and other vitamins, such as e.g. vitamin B or vitamin A, metal ions, such as e.g. $Fe^{2+}$ or $Cu^+$, phenolic compounds, such as e.g. phenol carboxylic acids or flavonoids, organic acids, proteins, polypeptides, amino acids, alcohols, such as e.g. ethanol, and salts, such as e.g. $CaCl_2$.

In one preferred embodiment, the antioxidative compound is $SO_2$.

In one preferred embodiment, the antioxidative compound is ascorbic acid.

In one preferred embodiment, the oxidative compound is oxygen.

In one preferred embodiment, the phenol carboxylic acid is gallic acid.

In one embodiment, $SO_2$ is added to the sample and a quotient $BAX_{(sp)}$ of the rise in the EAP in the sample and the content of $SO_2$ in the sample is determined according to the following formula:

$$BAX_{(sp)} = \Delta EAP / \Delta SO_2 \text{ content}_{(sp)} [\text{min} \cdot \text{l/mg}]$$

in which $\Delta EAP$ is the EAP value after the addition of $SO_2$ minus the EAP value before the addition of $SO_2$, and in which $\Delta SO_2$ content is the $SO_2$ content brought about as a result of the addition.

In an alternative embodiment, a quotient BAX of the total EAP in the sample and the total content of $SO_2$ in the sample is determined according to the following formula:

$$BAX = EAP_{(total)} / SO_2 \text{ content}_{(total)} [\text{min} \cdot \text{l/mg}]$$

The object of the present invention is also achieved by the use of the method of the present invention for assessing the oxidative stability of a sample, preferably a beverage sample, preferably selected from the group consisting of a sample of beer, wine, juice and mixtures thereof.

The object of the present invention is also achieved by the use of a spin trap reagent for the qualitative and/or quantitative analysis of a stabilized secondary radical in a sample using ESR spectroscopy, wherein the spin trap reagent is suitable for making it possible to avoid the pH effect and the associated influence on the generation of radicals in the sample.

In one preferred embodiment of the use, the sample is a beverage sample selected from the group consisting of a sample of beer, wine, juice and mixtures thereof.

In a particularly preferred embodiment of the use, the sample is a beer sample.

In one preferred embodiment of the use, the spin trap reagent is POBN.

In one preferred embodiment of the use, the concentration of the spin trap reagent in the sample is approximately $\leqq 10$ mM.

In one particularly preferred embodiment of the use, the concentration of the spin trap reagent in the sample is approximately 3 mM.

In one preferred embodiment of the use, the spin trap reagent is soluble in the sample and preferably is dissolved in the sample.

In an alternative embodiment of the use, the spin trap reagent is dissolved in an aqueous ethanol solution or another aqueous solution before being added to the sample.

In one embodiment, the secondary radical is a hydroxyethyl radical.

The object of the present invention is also achieved by a kit for determining an EAP in a sample, comprising a spin trap reagent for the qualitative and/or quantitative analysis of a stabilized secondary radical using ESR spectroscopy, wherein the spin trap reagent is suitable for making it possible to avoid the pH effect and the associated influence on the generation of radicals in the sample.

In one preferred embodiment of the kit, the spin trap reagent is POBN.

In one preferred embodiment of the kit, the secondary radical is a hydroxyethyl radical.

The object of the present invention is also achieved by the use of the kit of the present invention for assessing the oxidative stability of a sample, preferably a beverage sample, preferably selected from the group consisting of a sample of beer, wine, juice and mixtures thereof.

The term "endogenous antioxidative potential" or "EAP" describes the antioxidative behavior of a sample and is based essentially on the totality of all compounds with an antioxidative effect which are present in a sample ($SO_2$, Maillard reaction products, ascorbic acid, phenolic ingredients, etc.).

The term "spin trap reagent" means a radical scavenger which stabilizes short-lived radicals. Suitable spin trap reagents are all those which make it possible to avoid falsifying the results according to the previous procedure of lag time measurement, in particular to avoid or eliminate the pH effect on the generation of radicals as a function of the PBN concentration, and thus to determine the "true" EAP of a sample, i.e. those which are able to ensure that the influence of the pH effect on the stabilized radical is negligible.

The term "stabilized secondary radical", or "stabilized radical" for short, means that a compound which stabilizes the radical, e.g. a spin trap reagent, has become attached. The term "secondary radical" encompasses the preferred hydroxyethyl radical but also those secondary radicals which are derived for example from fusel alcohols.

The term "ESR spectroscopy", as used here, refers to the carrying-out of an analysis by means of ESR spectroscopy, as known in the prior art.

The term "beer" encompasses all known types of beer, including alcohol-free beer. It also encompasses precursors of the finished beer, as produced for example in the course of the brewing process. The term "wine" encompasses all known types of wine, including cider and alcohol-free products. The term "juice" encompasses both fruit juices and vegetable juices. Sparkling wine, champagne and wine-containing beverages are also taken into account. Intermediate products formed during the wine and juice production process are also intended to be covered. Mixtures of the aforementioned beverages may be mixtures with water ("fruit juice drink") or carbonated mineral water ("spritzer"), mixtures of beer with lemonade ("shandy") or mixtures of fruit juice with spirits ("cocktail"). In principle, all drinks which have an EAP are considered.

The "oxidative stability" means the "beverage stability" or "beer stability", measured as the EAP value, which can be graded as follows: <100 min low stability, 100-300 min medium stability, 300-500 min high stability, >500 min very high stability. In principle, the EAP determination works in all ranges of oxidative beer stability. According to the present invention, the oxidative stability is an important factor which influences the change in flavor of a beverage.

The term "forcing test" refers to a procedure used to simulate beer aging in an experimentally accelerated manner.

With regard to the "pH" at which the forcing test is carried out, it is desirable to remain as close as possible to the pH of the sample. The spin trap reagent should not affect the pH or should affect it only very slightly. The pH of beer is usually between pH 4.1 and pH 4.5; an excessive rise in the pH very quickly leads to the range of accelerated radical generation. Other pH values are measured for mixed beer beverages, such as shandy for example, and most juices: for shandy e.g. pH 3.78, for fruit juice e.g. pH 3.43, while carrot juice has a pH >5.

The "presence of ethanol" in the forcing test or the concentration of ethanol (in % by volume), which is preferably present when carrying out the forcing test, depends on the sample to be analyzed: an ethanol concentration in the range from approximately 0.01-20% by volume is recommended when measuring wine for example, 0.01-10% by volume for example in the case of strong beer or wine spritzer, 0.01-6.0% by volume for example in the case of beer, and 0.01-3.0% by volume for example in the case of juice.

The wording "a system which promotes the generation of radicals" encompasses systems such as, for example, a "Fenton system" or an "X-ray system" (see also Example 1, 1.1.).

The present invention was based on the discovery that the previously known method for measuring the lag time of beer is unsuitable for many samples for reliably assessing the EAP of a beverage, preferably a beer. While in the case of beer samples with a low oxidative stability a direct relationship with the actual EAP can be established to a limited extent, in the case of samples which have a medium to high oxidative beer stability the differences between the measured lag time value and the actual conditions in the beer may be up to 600%. This is not a negligible value, but must instead be referred to as significant influencing which can no longer be tolerated for an analysis method. Since the differences are dependent not only on the effect on radical generation brought about by the addition of PBN (pH effect) but rather, as described, are influenced to varying degrees in all lag time ranges, for such beers it is no longer possible to establish a relationship with the EAP. To complicate matters, added to this is the fact that many ingredients with an antioxidative effect (e.g. phenolic substances, ascorbic acid, etc.) are pH-dependent with regard to their action.

The present invention provides an improved method for assessing the oxidative stability of beverages, preferably beer, which makes it possible to detect the actual ("true") EAP in a sample by measuring the generation of secondary radicals, preferably hydroxyethyl radicals. The measurement method uses ESR spectroscopy and is based, like previously known methods, on an indirect detection of the radicals with the aid of a spin trap reagent. The radicals are preferably produced from the radical reactions of the primary oxygen radical species ($O^-_2 \cdot$; $OH \cdot$; $H \cdot$; $HO_2 \cdot$) with the different ingredients in the beverage, in particular alcohols. Unlike in the prior art, however, the method according to the invention uses special spin trap reagents which have very specific properties, with the spin trap reagent preferably being N-tert-butyl-α-(4-pyridyl) nitrone N-oxide (POBN). The properties of the spin trap reagent which are essential for the new EAP determination include, compared to the previous procedure, a much higher affinity for the secondary radicals, in particular the hydroxyethyl radicals, a higher stability of the spin trap reagent and of the spin trap adducts compared to the previous inactivation reaction which changed the pH, and the direct solubility of the spin trap reagent in the sample. By combining these properties with a targeted adaptation of the analysis parameters (e.g. forcing test at increased temperature, spin trap concentration, etc.), it is possible to determine the "true" EAP of a sample without significantly changing the existing conditions in a sample (pH, generation of radicals, etc.). The final criterion for the EAP in a sample under the defined experimental conditions is a value (EAP value) determined by the time at which unhindered radical generation starts in the sample.

As a result of the research work on which the present invention is based, and using a special radical-generating structure (Fenton system) and irradiation experiments (X-ray radiation to generate radicals), it was possible to clearly demonstrate that hydroxyl radicals are directly detected only to a slight extent during the lag time measurement. Instead, the signal intensity of the ESR spectra is caused mainly by the secondary hydroxyethyl radical, which obviously forms much more stable PBN spin adducts. Via the accumulation of these stable PBN—$C_2H_5O \cdot$ spin adducts during the measurement, the proportion of unstable PBN spin adducts in the overall spectrum becomes increasingly lower, until the signal intensity is caused almost exclusively by the PBN—$C_2H_5O \cdot$ spin adducts. Based on this fundamental finding, some relationships with regard to the lag time measurement of a beer can be explained, e.g. a higher signal intensity of the ESR spectra brought about as a function of the ethanol concentration (EtOH effect). The lag time measurement according to the previous procedure is a rather indirect determination of the generation of radicals in the beer, which leads to significant falsifications.

The method of the present invention has various advantageous over previously known methods.

First, the newly used spin trap reagent POBN has a much higher affinity for the secondary radicals, in particular hydroxyethyl radicals, as a result of which the quantity of reagent required for a reliable measurement is much lower (about 15 times lower) than the previously used PBN. Not only does this lead to a cost saving, but it also reduces by a multiple the possible influence that the spin trap reagent can have on the sample.

Second, both the spin trap reagent POBN and its spin trap adducts, in particular the POBN-hydroxyethyl radical adducts, are very stable and have a higher stability with regard to the inactivation reaction which changes the pH.

Third, the combination of the higher stability with regard to the inactivation reaction which changes the pH and the 15-times-lower concentration makes it possible to practically avoid the acceleration of the generation of radicals which was brought about in the previous method as a result of the pH effect caused by PBN.

Fourth, the fact of avoiding the pH effect ensures that the pH-dependent action of various ingredients with an antioxidative effect (phenolic substances, ascorbic acid, etc.) corresponds to the conditions that exist in a beer sample or another beverage sample.

Fifth, the fact of avoiding the pH effect together with the high resolution of the new measurement method additionally ensures that it is possible to clearly detect the action of certain ingredients (see $SO_2$ dependence) in a detailed and logical manner.

Sixth, since POBN, unlike e.g. PBN which has to be dissolved in an ethanol solution, is directly soluble in beer and other alcohol-containing beverages, it is possible to avoid any influencing of the measurement results by additional solvents. On the other hand, a preliminary dissolving of POBN in a water/ethanol solution or another aqueous solution, e.g. as a stock solution, should in no way be ruled out. In the case of beverages which are substantially alcohol-free, such as e.g. juices or alcohol-free beer, an exogenous addition of ethanol in the range from 0.01-5% by volume, preferably 3% by volume, should take place. In this way, the signal intensity of the stabilized secondary radicals is amplified and the evaluation is made easier.

Seventh, due to the proven linear dependence of the EAP values on the $SO_2$ content, it is possible by suitable addition to increase the EAP value relative to one mg $SO_2$ content, in order thus to define a new parameter. This parameter shows the effects of additional factors on the oxidative stability of beer and other beverages (metal ions, pH of the sample, other ingredients with an antioxidative effect, etc.). For example, it is possible to demonstrate the characteristics of different types of beer with regard to their antioxidative behavior and the differences between individual beers. For many beers in which the EAP is defined mainly by the $SO_2$ content, this parameter can be determined to a first approximation by the quotient between the measured (determined) EAP value in the sample and the total content of $SO_2$.

Eighth, due to the elimination of the falsifications according to the previous procedure, compared to the previous method the new EAP determination is additionally characterized by a much higher resolution of the results in the medium to high range of oxidative beverage stability. This allows a very detailed description of the negative or positive effects on the EAP of a beer or beverage. This is of critical importance for practical use.

With regard to practical use during the production and quality control of beer, the method of the present invention can be used to demonstrate the effects of the individual intermediate stages of the brewing process on the oxidative beer stability. By way of example, it is possible to check and demonstrate the effects on the EAP caused by fermentation, storage in storage tanks, chemico-physical beer stabilization (e.g. by silica gel or polyvinylpolypyrrolidone, PVPP) and individual filtration stages and bottling processes.

By means of the new EAP determination, the not inconsiderable costs of the spin trap reagents can be reduced by up to 80%. Compared to the previous method, the use of the new EAP determination when used routinely would save 12,000-15,000 Euro per year (saving per measurement approx. 7 Euro; lag time determination using 50 mM PBN/20 ml sample compared to EAP determination using 3 mM POBN/20 ml; 40 measurements per week; 50 measurements per year).

For the breweries, which will in future make routine use of EAP determination, the greater reliability of the EAP values not only provides the possibility of detecting inconsistencies in the brewing process in good time and then of taking appropriate action, but additionally provides an appreciable cost reduction with regard to quality control and quality assurance.

Another field of use for the new EAP determination results directly from the effect of the packaging materials on the oxidative beverage stability. Due to the high resolution of the results, the new EAP determination is suitable for comparing with a high level of accuracy the effects on the oxidative beverage stability caused by the oxygen permeation through the various packaging materials, such as e.g. plastic bottles, in particular made from PET or PEN, or bottles with oxygen barrier layers, and closure devices, such as e.g. crown caps, compound masses with $O_2$ scavenger properties, different types of clip closure (3-component, DIN, spherical head) or plastic closures, and comparing them with regard to their suitability (quality) for maintaining the oxidative beverage stability.

Unlike the previous determination method by means of PBN, which is unsuitable for detecting the EAP of a beer in a non-falsified manner, the high reliability and resolution of the EAP determination will in future be used to realistically describe the oxidative stability of beer and other beverages.

DETAILED DESCRIPTION OF THE INVENTION

The present invention will be explained in more detail on the basis of the following examples and in connection with the appended figures.

FIG. 1 shows the results of the measurements concerning the stability of the hydroxyl or hydroxyethyl radicals (PBN spin adducts) "trapped" by PBN.

FIG. 1A shows the stability of the PBN spin adducts ("trapped" hydroxyl or hydroxyethyl radicals) in a 0.1 M phosphate buffer (pH=4) after generation via a Fenton PBN system [$FeSO_4.7 H_2O$ 0.002 g/5 ml; PBN (25 mM) 0.0245 g/5 ml; $H_2O_2$ (30%) 0.025 ml/5 ml—special apparatus with mixing cell] without (a) and with EtOH 3.0% by volume (b) over time.

FIG. 1B shows the rise in signal intensity of the PBN spin adducts (water/EtOH solution) with the EtOH concentration after X-ray irradiation for the generation of radicals.

FIG. 1C shows the ESR spectra of the PBN spin adducts 5 min after the X-ray irradiation for the generation of radicals, with 5.0% by volume EtOH and without the addition of EtOH.

FIG. 2 shows the pH-dependent generation of hydroxyl radicals in the Fenton reaction.

Figure 7:
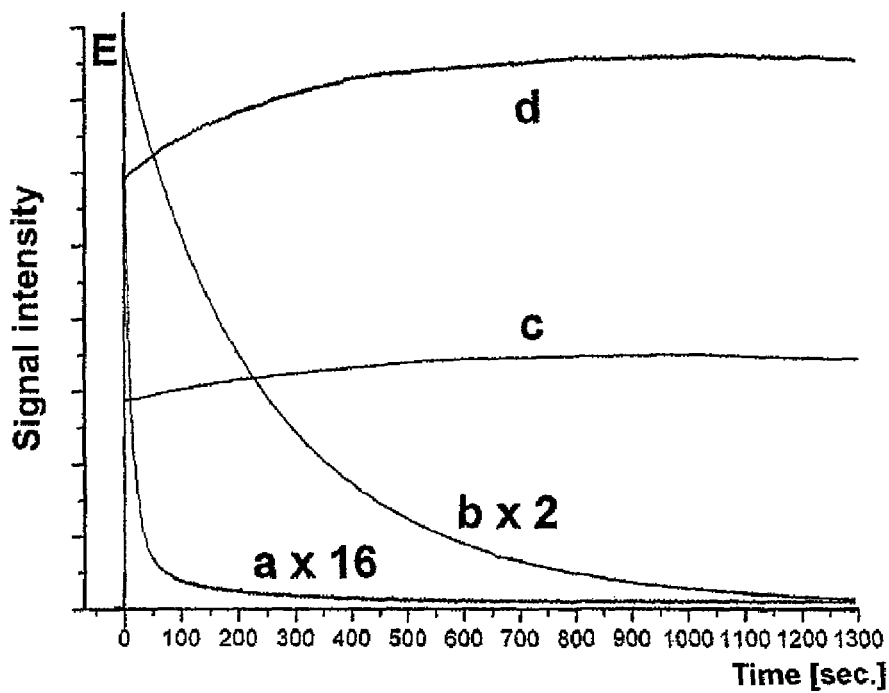

FIG. 7 shows a direct comparison of the results of the measurements concerning the stability of the hydroxyl and hydroxyethyl radicals (spin trap adducts) "trapped" by PBN and POBN in a 0.1 M phosphate buffer (pH=4) after generation via a Fenton PBN or Fenton POBN system [$FeSO_4.7 H_2O$ 0.002 g/5 ml; PBN (25 mM) 0.0245 g/5 ml; $H_2O_2$ (30%) 0.025 ml/5 ml—special apparatus with mixing cell] without (a, b) and with EtOH 3% by volume (c, d) over time.

Figure 8:
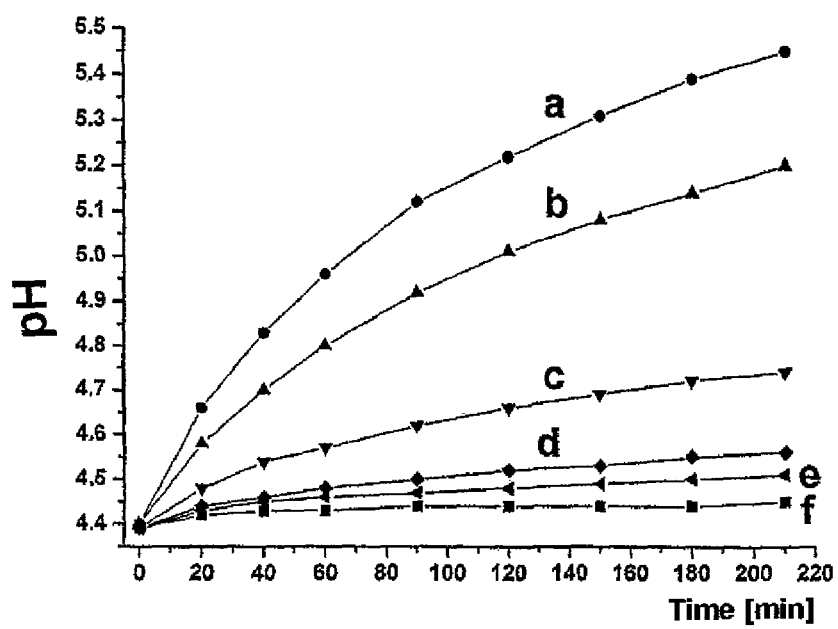

FIG. 8 shows the concentration-dependent influence, occurring in the context of a measurement to determine the EAP of a beer sample, of the spin trap reagents PBN and POBN on the pH curve (pH effect on the generation of radicals) (8a. 50 mM PBN; 8b. 30 mM PBN; 8c. 30 mM POBN; 8d. 10 mM POBN; 8e. 5 mM POBN; 8f. without spin trap addition).

FIG. 9 shows the results of the EAP determination by means of POBN in direct comparison with the previously customary lag time measurement (PBN) for the range of medium (FIG. 9a) and the range of medium to high oxidative beer stability (FIG. 9b).

FIG. 9A Sample: "Warsteiner" Pils (A): lag time measurement with 30 mM PBN; forcing test 63° C.; lag time=83 min; (B): EAP determination with 3 mM POBN; forcing test 63° C.; lag time=200 min.

FIG. 9B Sample: "Licher" Pils (A): lag time measurement with 30 mM PBN; forcing test 63° C.; lag time=102 min; (B): EAP determination with 3 mM POBN; forcing test 63° C.; EAP value=336 min.

Figure 10B:
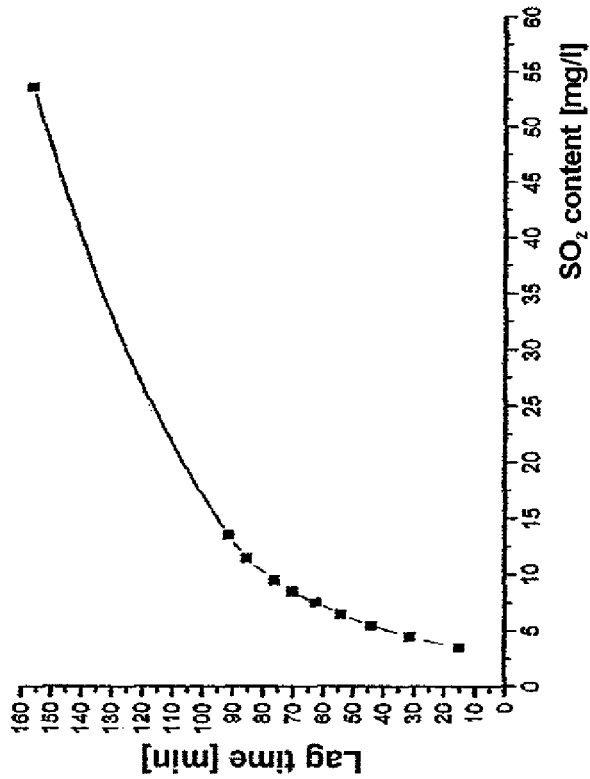
Figure 10A:
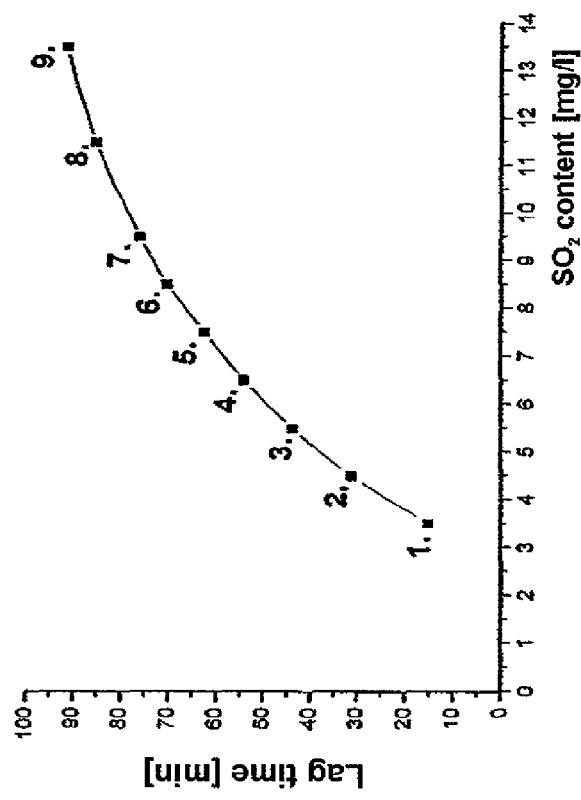
Figure 10C:
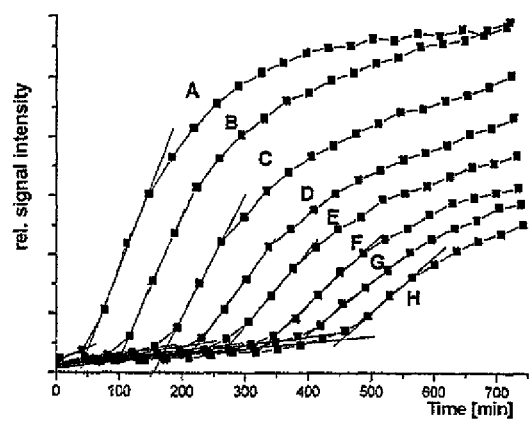

FIG. 10 shows the dependence of the lag time (FIG. 10A, B) and that of the EAP value (FIG. 10D) on the $SO_2$ content of a beer sample and also the evolution of the curves in the course of the EAP determination over the time of the forcing test (63° C.) for different $SO_2$ contents (FIG. 10C).

Figure 10D:
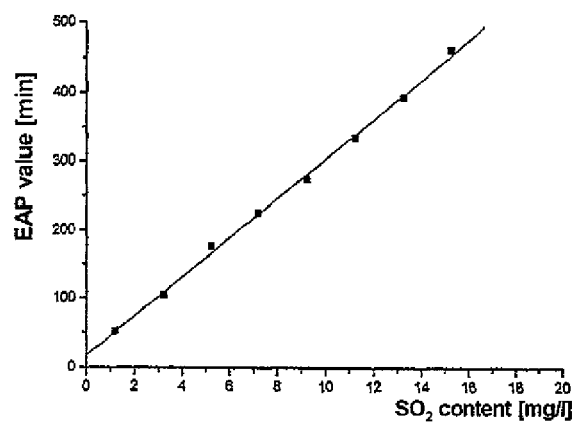
Figure 11:
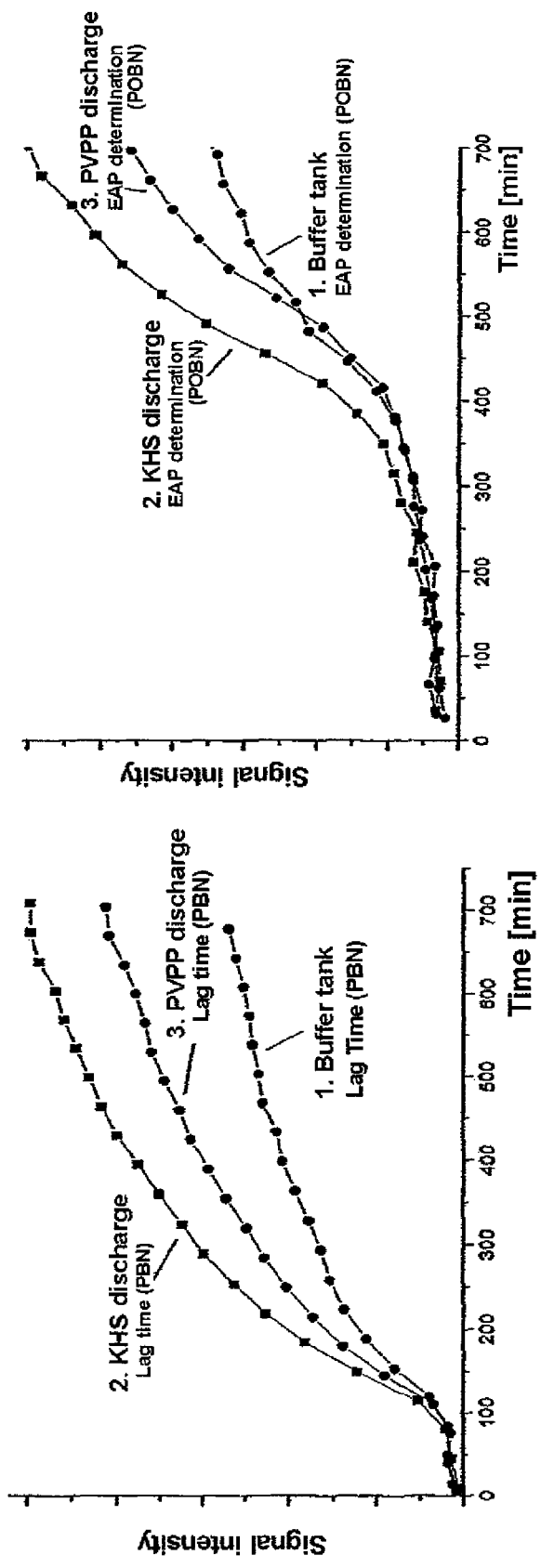
Figure 12:
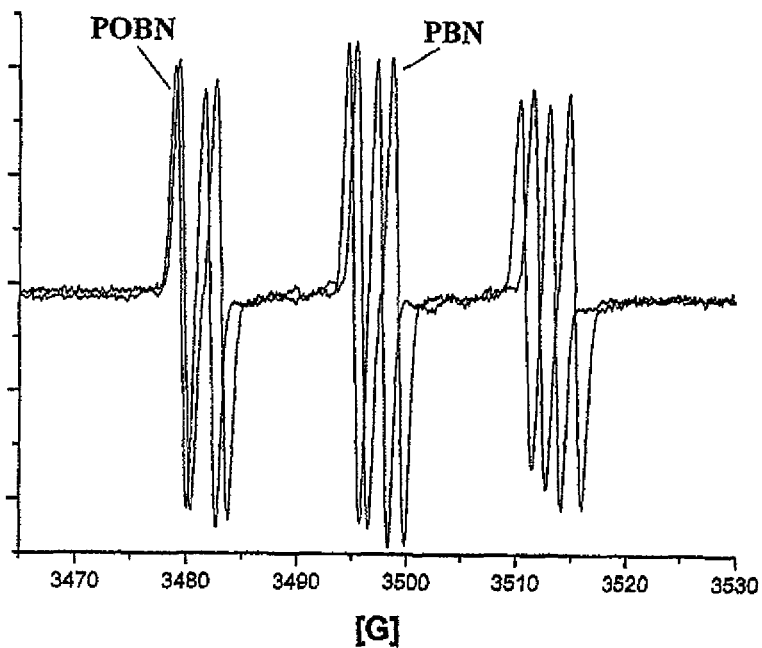
Figure 13:
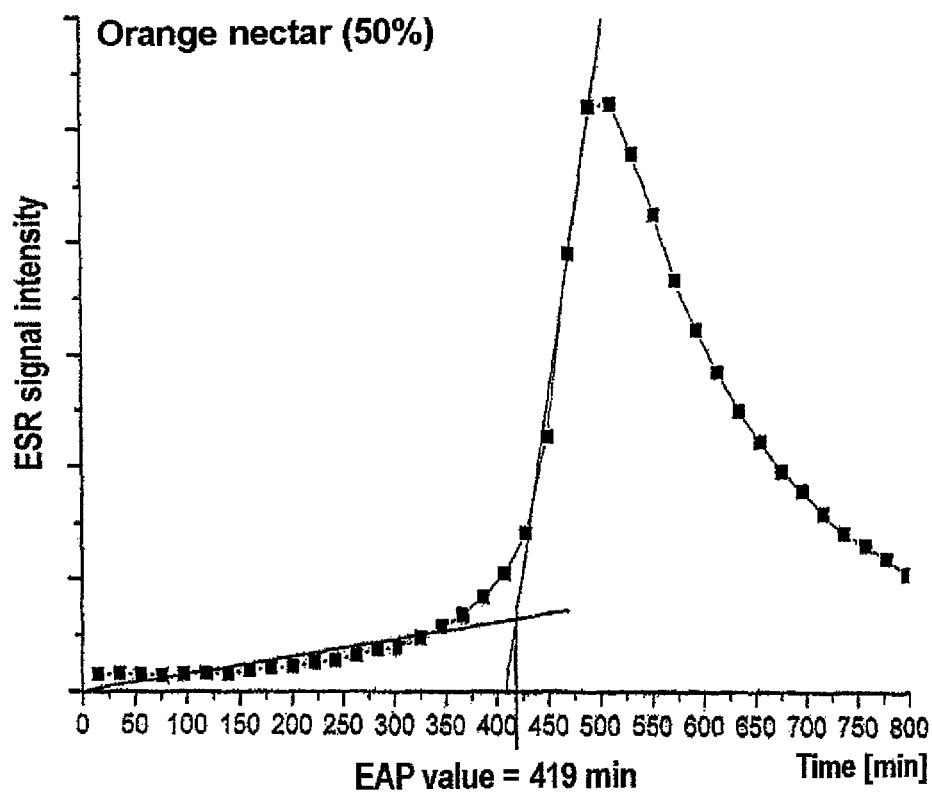
Figure 14:
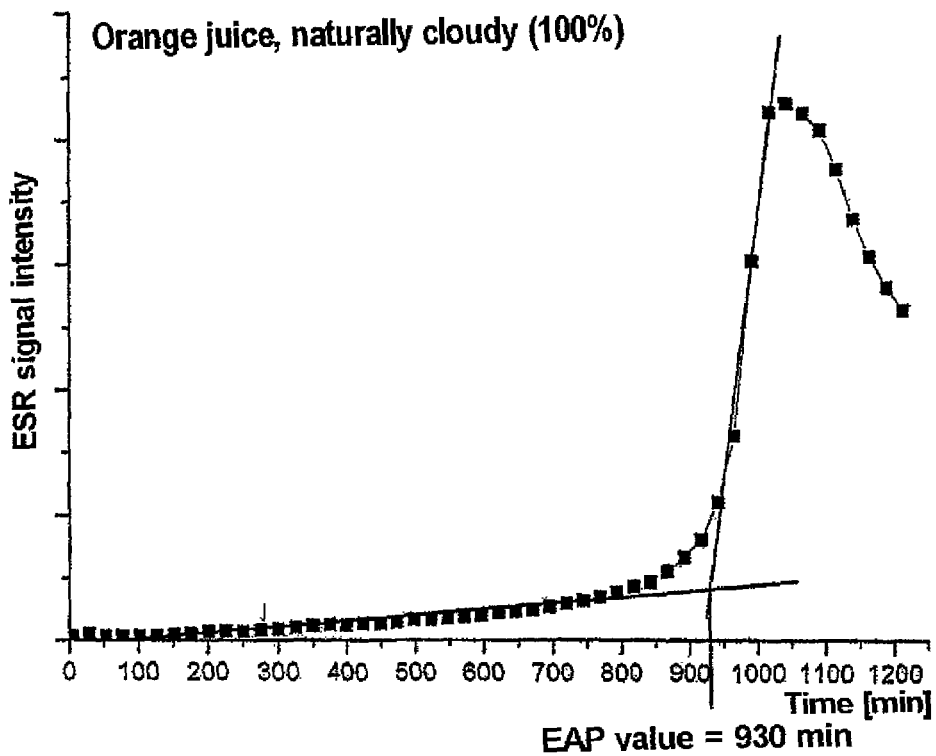
Figure 15:
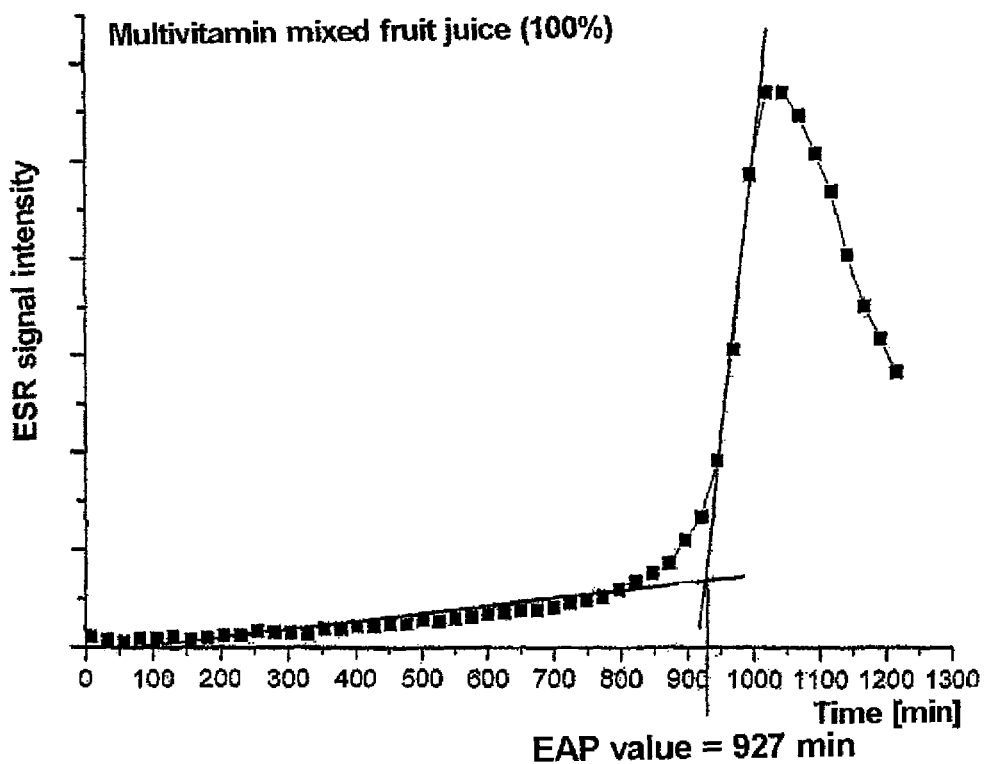
Figure 16:
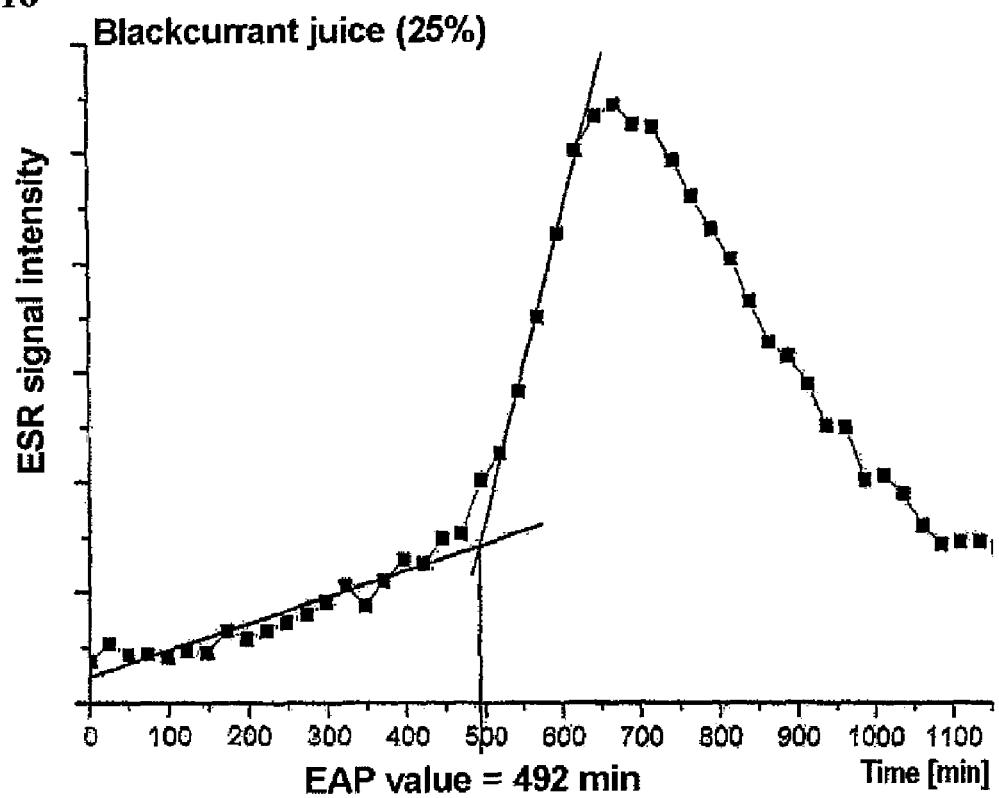
Figure 17:
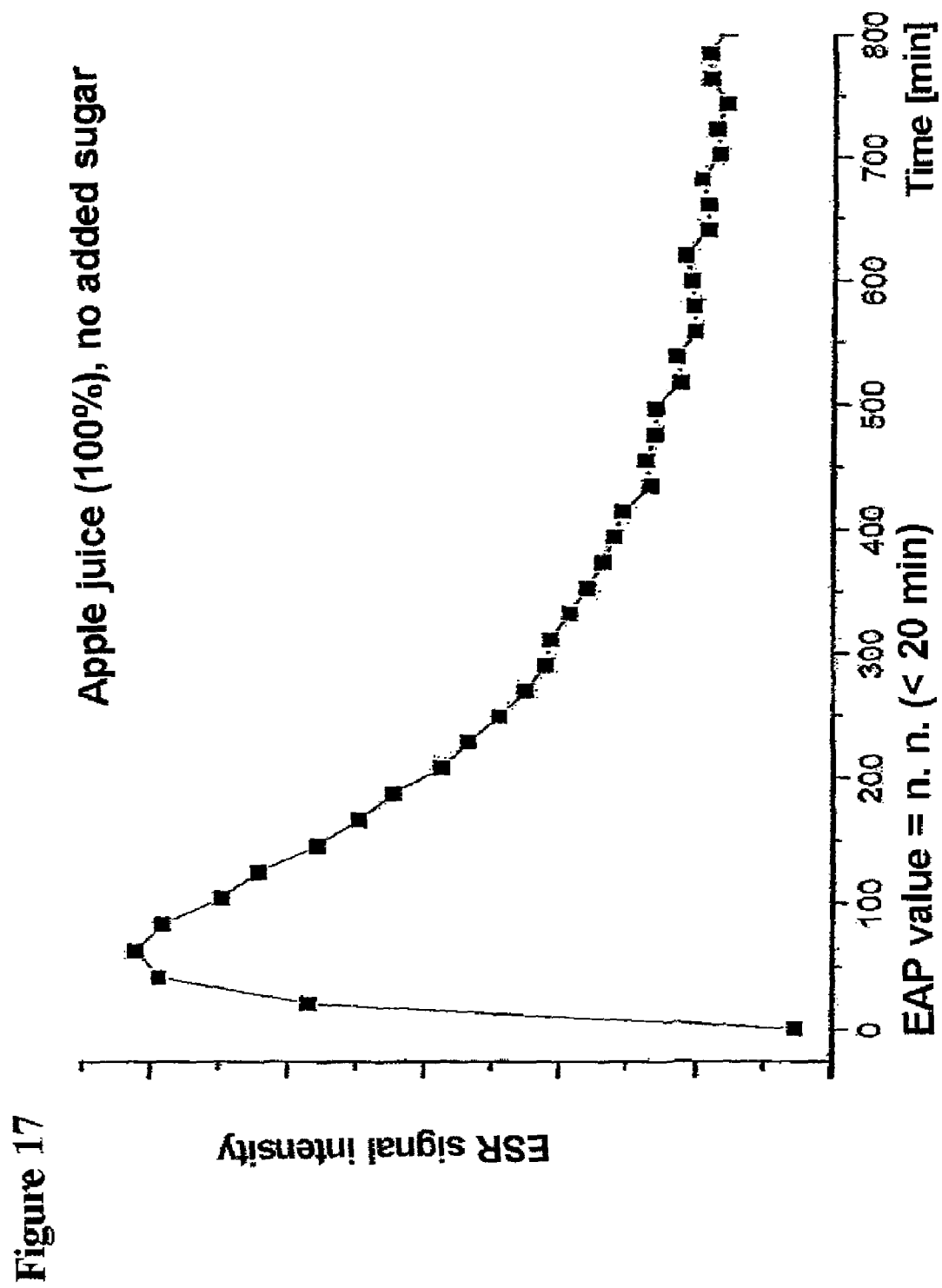
Figure 18:
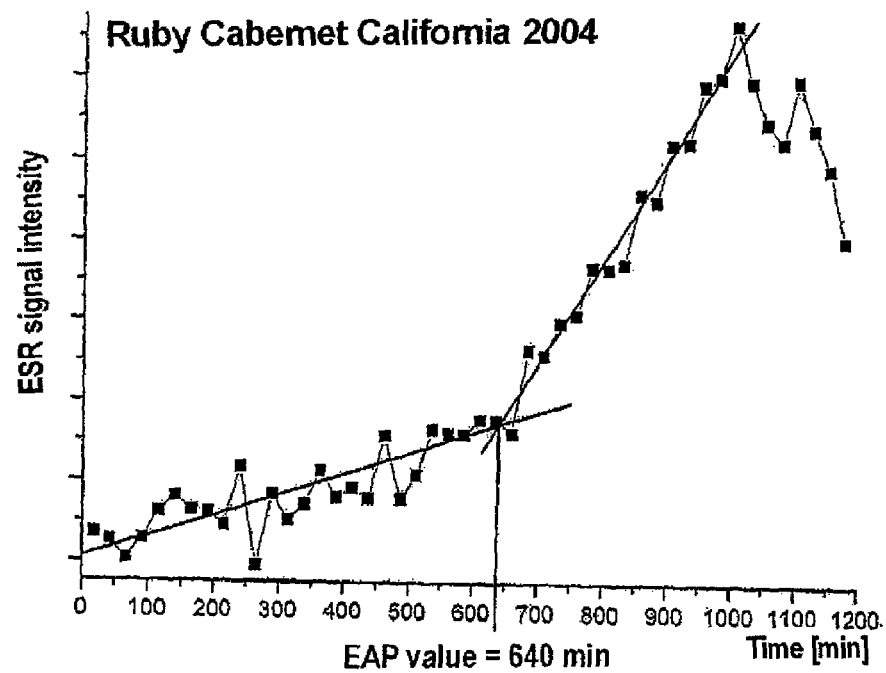
Figure 19:
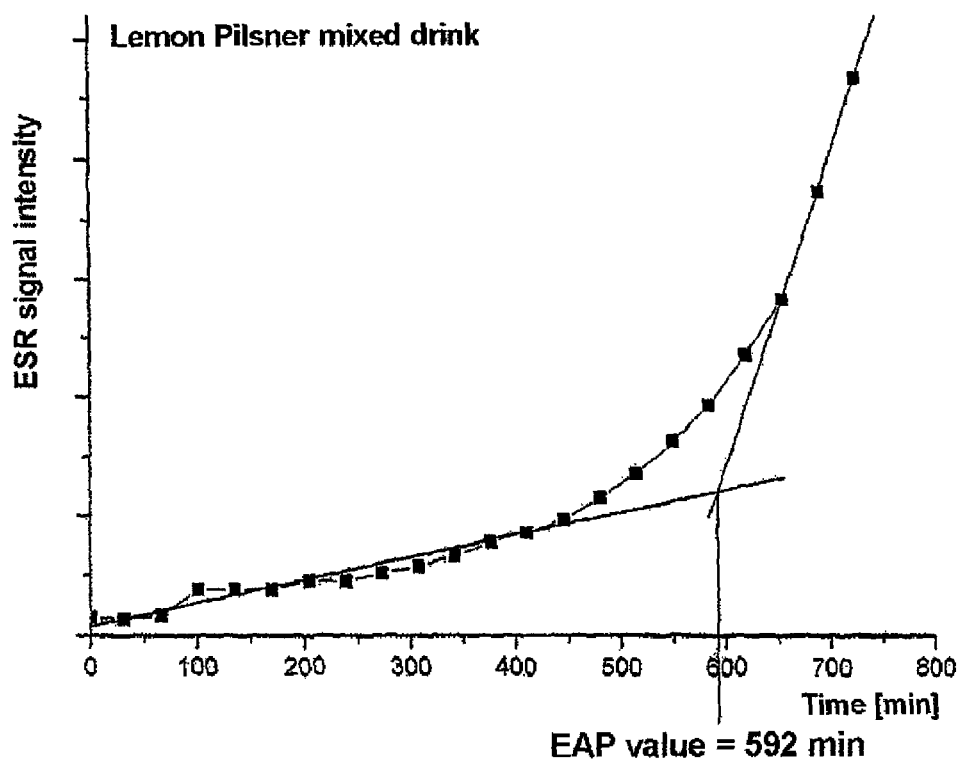

FIG. 10A 1. Lag time=15.0 min→$SO_2$ content=3.5 mg/l;
2. Lag time=31.2 min→$SO_2$ content=4.5 mg/l;
3. Lag time=43.8 min→$SO_2$ content=5.5 mg/l;
4. Lag time=54.1 min→$SO_2$ content=6.5 mg/l;
5. Lag time=62.5 min→$SO_2$ content=7.5 mg/l;
6. Lag time=70.3 min→$SO_2$ content=8.5 mg/l;
7. Lag time=76.0 min→$SO_2$ content=9.5 mg/l;

8. Lag time=85.3 min→$SO_2$ content=11.5 mg/l;
9. Lag time=91.4 min→$SO_2$ content=13.5 mg/l.
FIG. 10B Details as in FIG. 10A, plus:
10. Lag time=156 min→$SO_2$ content=53.3 mg/l.
FIG. 10C shows the evolution of the curves in the course of the EAP determination with a rising $SO_2$ content in a beer sample.
FIG. 10D A: EAP value=52 min→$SO_2$ content=1.2 mg/l;
B: EAP value=105 min→$SO_2$ content=3.2 mg/l;
C: EAP value=176 min→$SO_2$ content=5.2 mg/l;
D: EAP value=225 min→$SO_2$ content=7.2 mg/l;
E: EAP value=275 min→$SO_2$ content=9.2 mg/l;
F: EAP value=335 min→$SO_2$ content=11.2 mg/l;
G: EAP value=393 min→$SO_2$ content=13.2 mg/l;
H: EAP value=461 min→$SO_2$ content=15.2 mg/l.
FIG. 11 shows, based on the example of chemico-physical beer stabilization, the suitability of the EAP determination for detecting the effects of individual brewing process stages on the EAP of a sample.
FIG. 11A Lag time measurements by means of 50 mM PBN (forcing test 63° C.)
1. Buffer tank—(lag time—PBN)
2. KHS discharge=after chemico-physical beer stabilization by means of protein stabilization (silica gel)—(lag time—PBN)
3. PVPP discharge=after chemico-physical beer stabilization by means of polyvinylpolypyrrolidone—(lag time—PBN).
FIG. 11B EAP determination by means of 3 mM POBN (forcing test 63° C.)
1. Buffer tank—(EAP determination—POBN)
2. KHS discharge=after chemico-physical beer stabilization (protein stabilization with silica gel)—(EAP determination—POBN)
3. PVPP discharge=after chemico-physical beer stabilization by means of polyvinylpolypyrrolidone—(lag time—POBN).
FIG. 12 shows the ESR spectra of N-tert-butyl-α-phenylnitrone (PBN) and N-butyl-tert-α-(pyridyl)nitrone N-oxide (POBN).
FIG. 13 shows the use of EAP determination in the juice sector based on the example:
orange nectar (50%), ALDI, batch: M35 02:05 06.07, best before 30.06.06
ascorbic acid content—as provided by manufacturer: no information independent analysis: analysis of ascorbic acid in juices, method: HPLC, UV detection, MEBAK vol. II, 4th edition, 2002, 3.7.1.1.
ascorbic acid content: 122 mg/l
EAP value: 419 min (forcing test 60° C.).
FIG. 14 shows the use of EAP determination in the juice sector based on the example:
orange juice, naturally cloudy (100%), Frucht-Oase, ALDI, best before 30.06.06
ascorbic acid content—as provided by manufacturer: 320 mg/l
independent analysis: (for reference, see above)
ascorbic acid content: 351 mg/l
EAP value: 930 min (forcing test 60° C.).
FIG. 15 shows the use of EAP determination in the juice sector based on the example:
multivitamin mixed fruit juice (100%), Frucht-Oase, ALDI, best before 30.06.06 ascorbic acid content—as provided by manufacturer: 300 mg/l
independent analysis: (for reference, see above)
ascorbic acid content: 327 mg/l
EAP value: 927 min (forcing test 60° C.).
FIG. 16 shows the use of EAP determination in the juice sector based on the example:
blackcurrant juice (25%), Elmenhorster, ALDI, best before 01.06.06
ascorbic acid content—as provided by manufacturer: 250 mg/l
independent analysis: (for reference, see above)
ascorbic acid content: 159 mg/l
EAP value: 492 min (forcing test 60° C.).
FIG. 17 shows the use of EAP determination in the juice sector based on the example:
apple juice (100%) no added sugar, RIO DORO, ALDI, batch: b15Q126G22, best before 01.06.06
ascorbic acid content—as provided by manufacturer: no information independent analysis: (for reference, see above)
ascorbic acid content: 1.7 mg/l
EAP value: n.d. (<20 min) (forcing test 60° C.).
FIG. 18 shows the use of EAP determination in the wine sector based on the example:
Ruby Cabernet California 2004, 13.5% vol., ALDI, batch: 115.0741
EAP value: 640 min (forcing test 60° C.).
FIG. 19 shows the use of EAP determination in the mixed beer drink sector based on the example:
Lemon Pilsner mixed drink, Licher Fresh Lemon, 2.5% vol.
EAP value: 592 min (forcing test 63° C.).

EXAMPLES

Example 1

Measurement Method 1.1. Technical Equipment
The following ESR spectrometer was used for the lag time measurement by means of PBN and for the EAP determination by means of POBN:
Type: X-band spectrometer; Bruker (ESP-300); cavity type: Bruker 4108 TMH No.: 8603.
Type: X-band spectrometer; Magnettech Miniscope MS 100.
The irradiation experiments concerning the artificial generation of radicals (irradiation experiments FIG. 1B, C) were carried out by means of X-ray irradiation (X-ray tube from Seifert Debyflex).
The term "X-ray system" for the generation of radicals, as used here, describes the artificial generation of radicals via ionizing radiation (X-ray radiation), as known in the prior art.
The measurements concerning the stability of the spin trap adducts (PBN and POBN spin adducts, i.e. "trapped" hydroxyl and hydroxyethyl radicals) under the artificial generation of radicals by means of a Fenton system (FIG. 1A, FIG. 7) were carried out using a special apparatus developed and constructed in-house. With this special structure it is possible, using a mixing cell, to generate a Fenton system, i.e. a combination of hydrogen peroxide and metal ions ($Fe^{2+}$), in different solutions, directly in the measuring cuvette and to directly monitor the stabilization reaction with spin trap reagents or the decomposition of the adducts via the time sweep function of the ESR spectrometer (Bruker ESP-300, see above) (FIG. 1A, FIG. 7).

The term "Fenton system", as used here, refers to a reaction system in which the Fenton reaction is started in a targeted manner under experimental conditions by combining hydrogen peroxide and metal ions ($Fe^{2+}$) in different solutions. The Fenton system is used mainly for the artificial generation of radicals, in particular hydroxyl radicals.

1.2. Reagents

N-tert-butyl-α-phenylnitrone (PBN) 98%, $C_{11}H_{15}NO$, M=177.2 g/mol;

(SIGMA CHEMICAL CO., P.O. Box 14508 St. Louis, Mo. 63178 USA, Tel. 314-771-5750; SIGMA-ALDRICH CHEMIE GmbH P.O. 1120, 89552 Steinheim, Germany, Tel. 49-7329-970; No. B-7263, 5 g, batch 31K1498, at least 98% [3376-24-7], EC No. 222-168-6. "For RAD use only. Not for drug, household or other uses." W5/R).

N-tert-butyl-α-(4-pyridyl)nitrone N-oxide (POBN) 99%, $C_{10}H_{14}N_2O_2$, M=194.23 g/mol;

(SIGMA-ALDRICH CHEMIE GmbH P.O. 1120, 89552 Steinheim, Germany, Tel. 49-7329-970, 1 g, at least 99%, No. 215430, batch 01609KA, CAS No. 66893-81-0, Beil 145376, EC No. 266-512-3. "For RAD use only. Not for drug, household or other uses." W5/R).

Ethanol pro analysis 99.8%, $C_2H_5OH$, M=46.07 g/mol, density: 1 l=0.79 kg;

(Merck KgaA, 64271 Darmstadt, Germany, Tel. 49(0)6151 72-2440; EC No.: CE 200-578-6, batch K29301283125, No. 1.00983.1011, UN 1170, purity at least 99.8%, VbF B3.2 (IMDG code), use by 31.05.06, R: 11, pp.: 7-16).

Iron (II) sulfate heptahydrate 99.5%, $FeSO_4 \cdot 7H_2O$, M=278.02 g/mol;

(MERCK KGaA, 64271 Darmstadt, Germany, Tel. 49(0) 6151 72-2440, 1 kg, at least 99.5%, No. 1.03965.1000, batch: TA700665 951, EC No. CE231-753-5, R: 22 pp.: 24/25).

Hydrogen peroxide 30% (w/w)) $H_2O_2$, M=34.01 g/mol;

(MERCK Schuchardt OHG, 85662 Hohenbrunn, Germany, Tel. 49(0)810 2 802-0, 1 l, No. 8.22287.1000, batch: K33213287 420, EC No. 2317650 R: 34 pp.: 3-26-36/37/39-45).

Sodium sulfite, anhydrous, pro analysis; $Na_2SO_3$; M=126.04 g/mol; density: 2.63 g/cm³ (20° C.)

MERCK Art. No: 106657; CAS number: 7757-83-7; poison class CH: 3—strong poisons; HS store number: 28321000; EC No.: 231-821-4; Storage class (VC1): LGK 10-13; Storage: no restriction; water hazard class: 1—slightly hazardous to water; disposal: 28.

1.3. ESR parameter settings used

Figure 3:
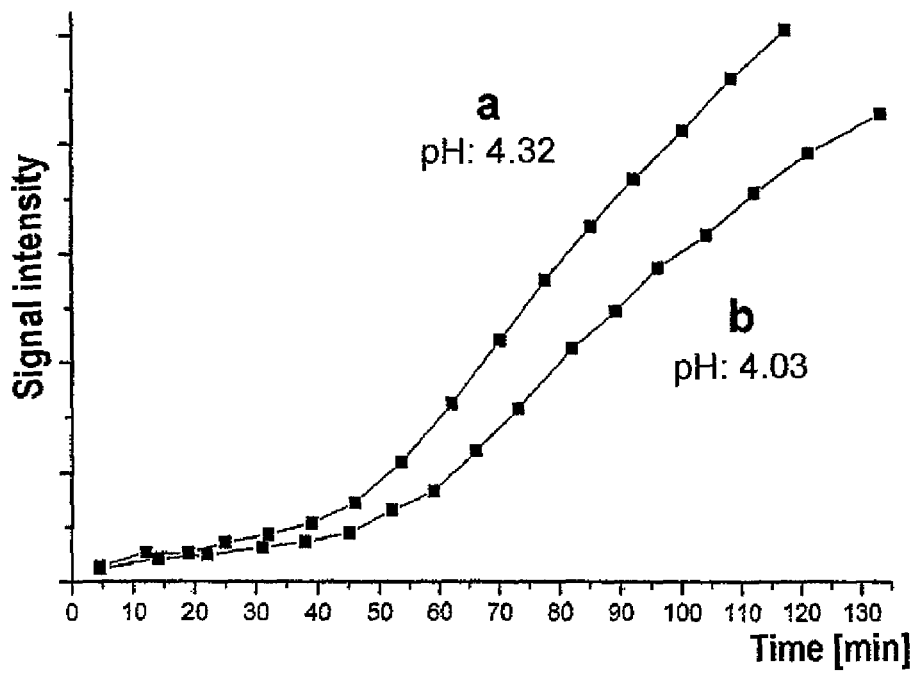
FIG. 3 shows the dependence of the lag time determination by means of PBN on the initial pH of the beer sample in the forcing test at 60° C. (3a. pH=4.32, lag time=46.7 min; 3b. pH=4.03, lag time=53.2 min).
Figure 5:
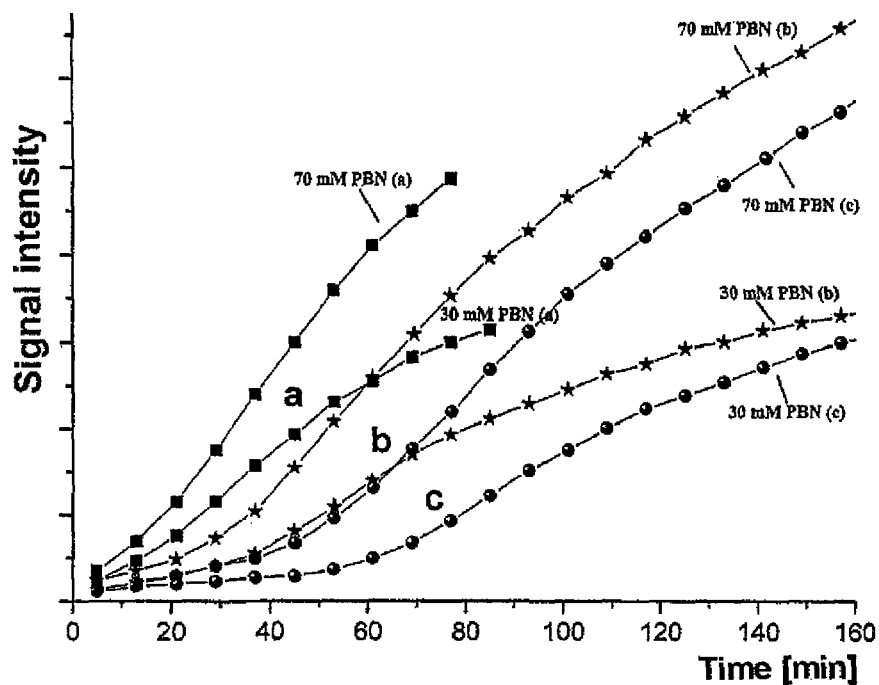
FIG. 5 shows the diverging curves and lag time values between different PBN concentrations (30 mM and 70 mM PBN) as a function of the EAP of a beer sample for the range from a low to medium oxidative beer stability (5a. 70 and 30 mM PBN in the low range; 5b. in the low to medium range; 5c. in the medium range of oxidative beer stability).
Figure 6:
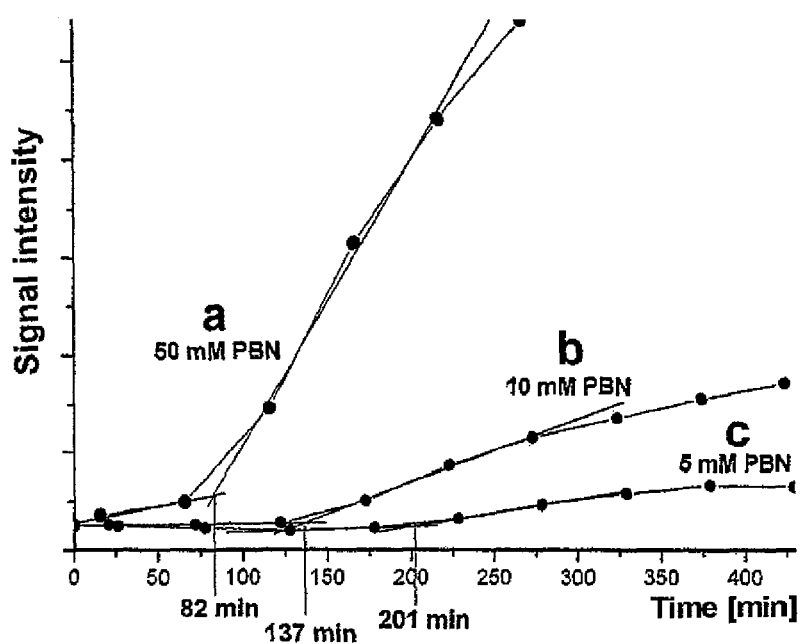
FIG. 6 shows the lag time loss caused by the PBN concentration in the range from medium to high oxidative beer stability for the PBN concentration range of 5, 10 and 50 mM (forcing test 63° C.; 6a. 50 mM PBN→lag time~82 min; 6b. 10 mM PBN→lag time~137 min; 6c. 5 mM PBN→lag time~201 min).

Measurements of the results shown in FIG. 1A:

Type: X-band spectrometer; Bruker (ESP-300), Sweep Time Function (2 Peak): Center Field: 3500 [G]; Attenuation: 10 dB; Phase: 0 [deg]; Conversion Time: 320.00 ms; Time Constant: 163.84 ms; Data Points: 4096; Number of Scan: 1; Sweep Time: 1310.7 ms; Receiver Gain: (a)=4·104/(b)=2.5·103; Mod. Ampl.: 0.1 [mT]; Mod. Frequency: 100 kHz; Cavity Type: Bruker 4108 TMH No.: 8603;

Measurements of the results shown in FIG. 1B, C:

Type: X-band spectrometer; Bruker (ESP-300), Center Field: 3504 [G]; Attenuation: 10 dB; Conversion Time: 40.96 ms; Phase: 2 [deg]; Time Constant: 40.96 ms; Receiver Gain: 1·105; Sweep Width: 7.0 [mT]; Data Points: 1024; Number of Scan: 10; Mod. Ampl.: 0.1 [mT]; Mod. Frequency: 100 kHz; Cavity Type: Bruker 4108 TMH No.: 8603;

Measurements of the results shown in FIGS. 3, 5, 10A, B:

Type: X-band spectrometer; Bruker (ESP-300); Center Field: 3500 [G]; Attenuation: 10 dB; Conversion Time: 40.96 ms; Phase: 0-5 [grd]; Time Constant: 40.96 ms; Receiver Gain: 1·105; Number of Scan: 3; Sweep Width: 7.0 mT; Mod. Ampl.: 0.1 [mT]; Mod. Frequency: 100 kHz; Data Points: 1024; Number of Scan: 3; Cavity Type: Bruker 4108 TMH No.: 8603;

Measurements of the results shown in FIGS. 6, 9A, B, 10C, D, 11A, B:

Type: X-band spectrometer; Magnettech Miniscope MS 100; Center Field: 3352 [G]; Attenuation: 3 dB; Sweep Time: 40 sec; Sweep Width: 24 [G]; Receiver Gain: 300; Phase: 180 [grd]; Mod. Ampl.: 1 [G]; Number of Scan: 3; Mod. Frequency: 100 kHz; Data Points: 1024;

Measurements of the results shown in FIG. 7:

Type: X-band spectrometer; Bruker (ESP-300); Sweep Time Function (2 Peak): Center Field: 3500 [G]; Attenuation: 10 dB; Phase: 0 [deg]; Conversion Time: 320.00 ms; Time Constant: 163.84 ms; Data Points: 4096; Number of Scan: 1; Sweep Time: 1310.7 ms; Receiver Gain: (a)=4·104/(b)=5·103/(c)=2.5·103/(d)=2.5·103; Mod. Ampl.: 0.1 [mT]; Mod. Frequency: 100 kHz; Cavity Type: Bruker 4108 TMH No.: 8603.

1.4. Carrying Out the Measurement 1.4.1. General Procedure Based on the Example of Beer Individual sample: 12 ml beer+optionally EtOH (e.g. 0.1 ml)+0.15 ml POBN solution→sample volume=12.25 ml (14 samples in total).

In the case of beer, which usually has an alcohol content of approx. 5.0% by vol., the measurement can also be carried out without the addition of EtOH. The spin trap reagent POBN is soluble in beer and can also be added directly. The example describes only a practice-oriented implementation which omits the weighing-out for each individual sample.

Batch of POBN solution for a 3 mM POBN concentration in the total sample volume:

POBN 194.23 g/mol (99%): 194.23 g/mol/99%·100%=196.2 g/mol 196.2 mg/mmol/1000 ml·12.25 ml/sample·3 mM=7.21 mg/sample 14 samples in total→14·7.21 mg/sample=100.94 mg;

100.94 mg (POBN 99%) dissolved in 2.1 ml (14·0.15 ml) of distilled $H_2O$;

Method Steps:

(a) providing the sample;

(b) adding 0.1 ml EtOH+0.15 ml POBN solution;

(c) carrying out the analysis by means of ESR spectroscopy (forcing test 63° C.):

(ESR parameter setting—X-band spectrometer Bruker (e-scan): Center Field: 3467 [G]; Attenuation: 3 dB; Phase: 328.47 [deg]; Conversion Time: 20.480 ms; Data Points: 512; Time Constant: 81.92 ms; Number of Scan: 10; Sweep Time: 10.486 s; Receiver Gain: 3.17e+003; Mod. Ampl.: 1.18 [G]; Mod. Frequency: 86.00 kHz; Frequency: 9.776 GHz);

(c1) taking a sample (measurement sample) from the forcing test at a selected time interval or at a given time;

(c2) recording the ESR spectra of each individual measurement sample;

(d) evaluating the EAP value via the ESR individual spectra of all individual measurement samples;

(e) displaying the results via suitable software (e.g. ORIGIN).

The procedure when measuring mixtures of beer with other beverages (mixed beer drinks) corresponds largely to the procedure described above for beer. If the alcohol content is too low, e.g. in the case of mixtures of beer with alcohol-free beverages, then the addition of 0.01-3.0% by volume EtOH is recommended, depending on the mixing ratio. A similar addition of EtOH is also recommended in the case of non-alcoholic ("alcohol-free") beers.

1.4.2. Juice

The procedure when measuring juice corresponds largely to the procedure described above for beer (forcing test at 60° C. preferred).

For juices, an EtOH addition of 0.01-5.0% by volume (preferably 3.0% by volume) is recommended. This produces a higher signal intensity for the "trapped" secondary radicals and facilitates the evaluation. In the case of naturally cloudy juices with a very high fruit content, centrifugation of the juice samples is necessary (5000 rpm, 5 min) (forcing test at 60° C. preferred).

The curve (fall after maximum), which differs from that of beer, can be attributed in the case of juices to the lower pH (e.g. pH 3.2-3.6), as a result of which the stability of the spin trap adducts is reduced. For juices with a high pH (e.g. carrot juice), the curves are characterized by a further rise, in a manner analogous to beer.

1.4.3. Wine

The procedure when measuring wine corresponds largely to the procedure described above for beer. Since wine has a higher alcohol content, there is no need to additionally add EtOH. Due to the low pH, however, a somewhat higher spin trap concentration (5 mM POBN) is recommended.

Example 2

Detection of the Stability of the Hydroxyethyl Radical Adducts

Using a special radical-generating structure (Fenton system) and by means of irradiation experiments (X-ray radiation for generating radicals), it was possible to demonstrate that hydroxyl radicals are detected directly only to a slight extent in the case of lag time measurement. Instead, the signal intensity of the ESR spectra is caused mainly by the secondary hydroxyethyl radical, which obviously forms much more stable PBN spin adducts (FIG. 1). The shape of curve (a) in FIG. 1A shows that the stabilized hydroxyl adducts (PBN) formed after generation via a Fenton system (pronounced rise during the injection up to E) are almost completely broken down within one minute, while the hydroxyethyl adducts (PBN) produced in a Fenton system with the addition of EtOH remain practically unchanged even after 17 min (curve (b)). The additional rise in curve (b), i.e. the increase in signal intensity, can be attributed to the formation of further radicals (Fenton reaction), the reaction thereof with the EtOH and the high stability of the resulting PBN spin adducts. The further radical formation can also be observed in the curve of the Fenton PBN system without EtOH addition (curve (a)). The proportion of unstable PBN spin adducts (e.g. hydroxyl adducts) in the overall spectrum becomes increasingly small as the stable PBN—$C_2H_5O$. spin adducts accumulate in the course of the lag time measurement, until the signal intensity is caused almost exclusively by the PBN—$C_2H_5O$. spin adducts.

FIG. 1B shows the rise in the signal intensity of the PBN spin adducts (aqueous solution) with the EtOH concentration after X-ray irradiation for the generation of radicals, with the same irradiation duration and intensity.

FIG. 1C shows a comparison of the ESR spectra 5 min after irradiation of the aqueous PBN solution with and without EtOH. The typical triplet-from-doublet signals come from hydroxyethyl adducts (bottom, with addition of 5% by volume EtOH), while the hydroxyl adducts (top, without EtOH addition) produced by the irradiation have already reacted out.

Based on this fundamental finding, some relationships with regard to the lag time measurement of a beer can be explained, e.g. a higher signal intensity of the ESR spectra brought about as a function of the ethanol concentration (EtOH effect) [18].

Example 3

Dependence of the Lag Time Value on the Initial pH

Another aspect of the study was to determine the dependence of the measured lag time value on the various parameters of the forcing test. This is particularly important when an experimentally determined lag time value is to be correlated in a reproducible manner with the EAP or the flavor stability of a beer, which can be detected to a much less defined extent. It is important here to distinguish between the effects caused by the measurement method and the "real" effects brought about by the beer ingredients.

In this connection, reference is made in particular to the effect of the pH in the course of the lag time measurement [22]. According to Bishop et al. [19] and Millero et al. [20], a rise in the pH during the Fenton reaction, particularly in the pH range >4.5, leads to a considerable acceleration of the generation of hydroxyl radicals (see FIG. 2). It must be assumed that an acceleration in the generation of radicals also leads to the EAP of a beer being used up more quickly and to a corresponding reduction in the lag time value of a beer sample.

FIG. 3 shows corresponding measurement results obtained from beer samples with different initial pH values [16, 21]. As shown in FIG. 3, the lag time value determined from the curves changes considerably with the initial pH of the beer. In the case of a pH of 4.32 (curve (a)), the lag time is 46.7 min, whereas it is 53.2 min in the case of a pH of 4.03 (curve (b)). A change in the rise of the curves and in the final concentration of the spin adducts that is reached is also observed. Since the initial pH is below 4.35 (<4.5) for all the beer samples (cf. FIG. 3), i.e. the pH values are in a range in which the generation of radicals takes place relatively slowly (see FIG. 2), the overall relationship can be understood only once the significant influence of the spin trap reagent PBN on the lag time measurement is taken into account.

Example 4

Effect of the Spin Trap Reagent PBN on the pH Curve during the Lag Time Measurement The explanation regarding the deviation in lag time values in FIG. 3 results in principle from a pH effect, brought about by the spin trap reagent PBN [22], on the lag time measurement (pH effect in the forcing test at 60° C.).

Figure 4:
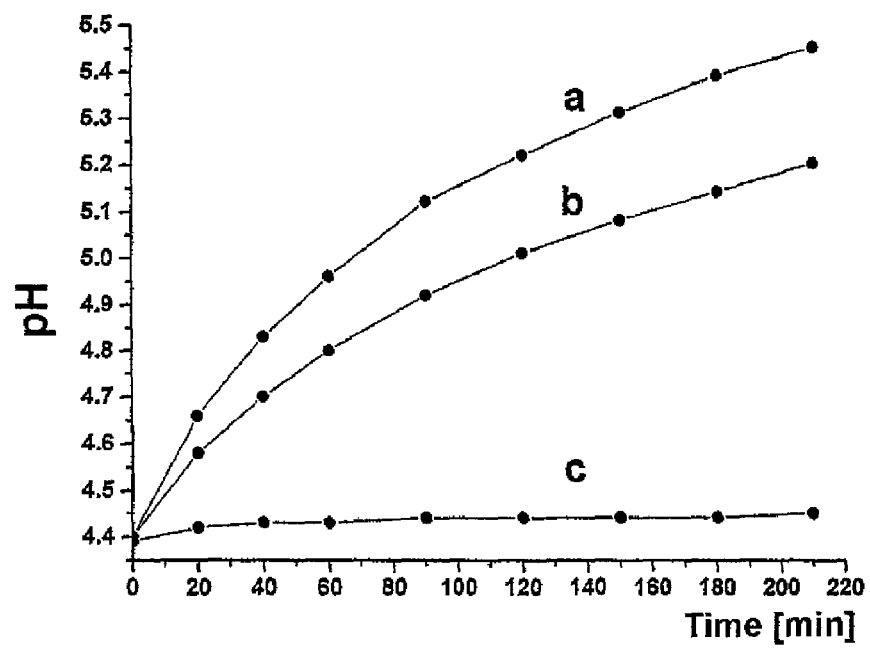
FIG. 4 shows the concentration-dependent influence of the spin trap reagent PBN on the pH curve in the context of a lag time measurement (pH effect on the generation of radicals) (4a. 50 mM PBN; 4b. 30 mM PBN; 4c. 0 mM PBN).

As can be seen from the measurement results in FIG. 4, curves (a) and (b), this pH effect leads to the situation where the pH of a beer sample rises over the total duration of the lag time measurement as a function of the PBN concentration used. The pH values of the beer samples in the case of a PBN concentration of 50 mM (curve (a)) and 30 mM (curve (b)) at the end of the lag time measurement (210 min) are therefore respectively 1 and 0.75 pH points higher than the pH of the beer sample without the addition of PBN (pH 4.45; curve (c)).

The measurements also showed that the rise in pH is practically independent of the existing EAP of a beer, i.e. it is caused exclusively by the PBN concentration used and can be explained by a reaction of the PBN which consumes $H^+$ ions and forms $OH^-$ ions.

This is a reaction in which the PBN concentration available for the stabilization of radicals is reduced to a certain degree via an inactivation reaction. Its cause very probably lies in a hydrolysis (benzaldehyde formation [22]) or an adduct formation after a previous protonation reaction. Here, the constantly increasing benzaldehyde odor in the course of the lag time measurement is in indication of how much the quantity of PBN used has been consumed via the inactivation reaction. The inactivation reaction is influenced by various parameters, such as e.g. temperature, pH and PBN concentration. Since the addition of PBN changes the generation of radicals via the pH in a concentration-dependent manner, the EAP of a beer is used up at different rates and the determined lag time value accordingly deviates, as a function of the PBN addition and the initial pH, from the actual EAP of a beer, i.e. the EAP of a beer is thus determined with a corresponding degree of falsification.

Example 5

Effect of the PBN Concentration on the Lag Time Value

The fact that there is a relationship between the measured lag time and the PBN concentration used has already been demonstrated by Uchida, M. et al. [1]. The higher the PBN concentration in a beer sample, the smaller the measured lag time value (FIG. 5).

If a given PBN concentration were always to give rise to a specific lag time loss, this deviation from the actual conditions in the beer could be tolerated, i.e. it would be possible to calculate the correct value.

However, the measurement results in FIG. 5 show that the lag time loss brought about by a certain PBN concentration, unlike the rise in pH (cf. FIG. 4), additionally depends on the existing EAP of a beer. In older beers with a low EAP and accordingly low lag time values, the difference brought about by a higher PBN concentration (70 mM compared to 30 mM) is relatively small (FIG. 5, curve (a)). If this result is compared with beer samples which have a higher EAP (FIG. 5, curves (b) and (c)), it can be seen that the difference in lag time brought about by the higher PBN concentration increases. Consequently, a deviation from the actual conditions in the beer results not only as the PBN concentration increases, but also as a function of the existing EAP of a beer sample.

This can be explained by the fact that the effect of the pH on the generation of radicals is different within the lag time due to the constantly increasing pH in the course of the lag time measurement. While the pH in the case of a PBN concentration of 50 mM rises only by 0.26 to 4.66 within a lag time of 20 min, after 60 min there has already been a pH rise by 0.56 to 4.96 (FIG. 4). Consequently, the generation of radicals within a high lag time is affected for a greater length of time and to a more pronounced degree—higher pH—in the direction of an increased formation of hydroxyl radicals. The existing EAP of a beer is therefore used up—relatively—quickly, and the measured lag time deviates more and more from the actual conditions in the beer (0 mM PBN).

From a direct comparison of the development of the pH in the case of a PBN concentration of 50 mM and 30 mM (FIG. 4, curves (a) and (b)), it can also be seen that the difference in pH between different PBN concentrations becomes greater in the course of the lag time measurement. This different change in pH and the temporally longer effect of higher pH values with increasing lag time values are responsible for the measured lag time differences diverging to an increasing extent at different PBN concentrations (FIG. 5).

In the case of beer samples characterized by a medium to high oxidative beer stability, the described deviations between the measured lag time value and the actual conditions in the beer may be up to 600%. This is not a negligible value, but instead must be considered as significant influencing.

For illustrative purposes, FIG. 6 shows the measurement results for a beer sample with a medium to high oxidative beer stability in the case of different PBN concentrations (50, 10, 5 mM) in the forcing test at 63° C. For beers with a higher oxidative beer stability, no lag time values could be obtained at a PBN concentration of 5 mM (inactivation reaction). Even for the medium to high lag time range, there is a difference of 119 min between a PBN concentration of 50 mM (lag time=82 min—starting value) and a PBN concentration of 5 mM (lag time=201 min).

It has nevertheless been shown that, while maintaining the same measurement conditions and using beer samples with the same EAP (e.g. same bottling) in the range of low to medium lag time values, the effects of different beer ingredients can also be demonstrated using the measurement method developed by Kaneda et al. [12] and Uchida et al. [1]. However, the direct comparison of the EAP of different types of beer, which possibly have different initial pH values and different alcohol contents, must be regarded as problematic and can lead to misinterpretations even in this range.

In the case of beers with a medium to high oxidative beer stability, the acceleration of the generation of radicals via the pH effect caused by the spin trap reagent PBN (FIG. 4, FIG. 5) is so significant that it is no longer possible to show or assess the actual differences in the oxidative beer stability of different beers by means of the lag time values. The lag time measurement in the previous form is therefore unsuitable for showing the EAP of a beer.

Example 6

Identification of a Suitable Spin Trap Reagent

Since ESR spectroscopy is the only measurement method which can be used to detect the radicals in the beer directly, it was necessary to develop a method which uses the properties of ESR to show the generation of radicals in the beer in a direct and non-falsified manner.

From a large number of measurement series, it was possible to select POBN (4-POBN, N-tert-butyl-α-(4-pyridyl) nitrone N-oxide) from the commercially available spin trap reagents. POBN was already assessed a number of years ago with regard to being used for lag time measurement, but was deemed to be unsuitable due to its high affinity for the hydroxyethyl radicals and its lower affinity for the hydroxyl radicals compared to PBN [e.g. 17]. Based on the results regarding the stability of the spin trap adducts of hydroxyl and hydroxyethyl radicals and their resulting proportion in the overall spectrum in the forcing test (60° C.) (ESR signal is caused mainly by "trapped" hydroxyethyl radicals instead of hydroxyl radicals), the method of the present invention uses precisely these properties of POBN, which had previously been deemed to be disadvantageous, to determine the EAP value.

The method of EAP determination according to the invention is based essentially on the use of more suitable spin trap reagents, preferably POBN, and also on a changed temperature during the forced beer aging (temperature range $\geq 40°$ C., preferably $\geq 60°$ C., more preferably 63-65° C., optimally 63° C.).

The principle here is based to a higher degree than before on the indirect detection of the generation of radicals in the beer by means of the very high affinity of the spin trap reagent POBN for the secondary radicals, in particular hydroxyethyl radicals (a reaction rate which is 15-20 times higher: POBN $3.1 \cdot 10^7$ $M^{-1}s^{-1}$ [23]; PBN $1.5 \cdot 10^6$ $M^{-1}s^{-1}$ [23]), which are produced mainly from the radical reactions of the primary oxygen radical species ($O^-_2$.; OH.; H.; $HO_2$.) with the ingredients of the beverage, preferably alcohols. In this way, it is possible to reduce the necessary spin trap concentration to a fraction of the previous concentration. This fact can be used in combination with the higher stability of the spin trap reagent POBN and its spin adducts relative to the inactivation reaction which changes the pH, with simultaneous targeted adaptation of the analysis parameters to the specific properties of POBN, to avoid the pH effect on the generation of radicals which existed in the previously used measurement method and to determine the actual "true" EAP of a sample.

Since POBN is also directly soluble in beer, it is possible to exclude the additional influencing of the measurement results by an addition of ethanol, for example brought about by the previously customary dissolving of PBN in an ethanol solution.

The final criterion for the EAP in a sample under defined experimental conditions is a value determined via the point in time at which the unhindered generation of radicals starts in the sample (EAP value).

Unlike the previous determination method by means of PBN, which is unsuitable for showing the EAP of a beer in a non-falsified manner, the high reliability and resolution of the new EAP determination can in future be used to realistically describe the oxidative beer stability and makes it possible to demonstrate the effects of the ingredients as such in a detailed manner.

FIG. 7 shows the measurement results for the POBN and PBN spin adducts in a special radical-generating Fenton system (0.1 M phosphate buffer, pH 4, cf. also FIG. 1A).

The shape of the curve (a) in FIG. 7 shows that the stabilized PBN-OH. adducts formed after radical generation (pronounced rise during the injection up to "E") are almost completely broken down within one minute, while the POBN-OH. adducts (curve (b)) have a stability that is $\approx 12$ times higher.

Although the higher stability of the hydroxyl radicals stabilized by POBN cannot be transferred in an equivalent manner to the conditions in a beer sample, it is nevertheless noticeable in the context of an EAP determination. The resulting proportion of stabilized hydroxyl radicals in the overall spectrum may lead to a certain scattering of the signal maxima in the course of the EAP determination, in particular in the lower curve (proportion of unstable spin trap adducts in the overall spectrum still relatively high).

This scattering can be avoided or reduced by scheduling a time buffer of approx. 3-4 min between the taking of the sample and the actual measurement. During this time, most of the unstable POBN spin adducts react out, and the signal intensity is defined mainly by the stable POBN—$C_2H_5O$. spin adducts in the lower curve too. The corresponding reaction can be understood based on an ESR spectrum recording via a number of scans at the start of an EAP determination (measurement directly after the taking of the sample in the start phase of EAP determination, lower curve).

From a direct comparison of the measurement results with the addition of ethanol (FIG. 7, curves (c), PBN, and (d), POBN), it can be seen that both spin trap reagents have a high stability in the case of the "trapped" hydroxyethyl radicals. The greater affinity of the spin trap reagent POBN for the hydroxyethyl radicals and the higher stability relative to the inactivation reaction which changes the pH is reflected in a higher total concentration of spin trap adducts (FIG. 7, curves (c) and (d)). The initial rise in signal intensity after the injection phase ("E") due to additional radical formation (Fenton reaction) behaves in an analogous manner.

The higher stability of the spin trap reagent POBN and its spin adducts (FIG. 7, curves (a), PBN, and (b), POBN) relative to the inactivation reaction which changes the pH becomes even more apparent when comparing the concentration-dependent pH curves of the two spin trap reagents during forced beer aging (60° C.) (FIG. 8).

It can be seen from the results in FIG. 8, curves (b) and (c), that the pH of a beer sample with a POBN concentration of 30 mM is subject to lesser influences compared to 30 mM PBN. This fact alone would result in coming closer to the conditions prevailing in the beer when using 30 mM POBN compared to the normally used concentration of PBN of 50 mM. However, even at a POBN concentration of 30 mM, the critical pH of 4.5 is exceeded [19, 20]. This means that only a falsified determination of the conditions that exist in the beer would be possible also in the case of a POBN concentration of 30 mM. Further measurements have also shown that the high affinity of the spin trap reagent POBN for the hydroxyethyl radicals leads to the situation where no useful results are obtained at a concentration of 30 mM (too quick a rise in the spin trap adduct concentration).

Only the combination of the two POBN properties makes it possible to determine the EAP of a beer, or also wine or fruit juice for example, directly and with a very high sensitivity.

On the one hand, the approx. 15-20 times higher affinity for the hydroxyethyl radicals is used to reduce the POBN concentration to a concentration of preferably 3 mM ($\leq 10$ mM). As a result, it is possible to carry out an EAP determination with a comparable signal intensity of the ESR spectra as was achieved in the previous lag time measurement with a PBN concentration of 50 mM.

On the other hand, the higher stability relative to the inactivation reaction which changes the pH leads to the situation where the pH of a beer sample at a POBN concentration of 3 mM rises by less than 0.03 pH points compared to a beer sample without the addition of POBN (FIG. 8, curves (e), 5 mM POBN, and (f), 0 mM POBN). Since this is also a pH range (<4.5) in which there are no appreciable effects on the rate of radical generation (see FIG. 2), the conditions that exist in the beer are practically achieved.

Example 7

EAP Determination in Direct Comparison with Lag Time Measurement

The finding discussed above is accordingly reflected in the measurement results of the EAP determination.

From the measurement results in FIG. 9, it is possible to see the significant difference between the previous lag time measurement and the EAP determination for the range of medium and medium to high oxidative beer stability. Even in the medium range of oxidative beer stability (FIG. 9), the effect on the generation of radicals brought about by the spin trap reagent PBN (30 mM) leads to the situation where the lag time value under the conditions of the forcing test (63° C.) deviates by approx. 2 h from the "true" conditions in the beer.

With regard to the lag time value, this corresponds to a deviation of 242% and can no longer be tolerated for an analysis method. The deviation in the range of medium to high oxidative beer stability (FIG. 9B) of approx. 4 h (328%) relative to the lag time values measured in the beer shows that the previous lag time measurement is unsuitable for determining the EAP of a beer. By using the normally used PBN concentration of 50 mM, this huge discrepancy is additionally amplified due to the faster rise in the pH (FIG. 8). Measurement results for beers with a very high oxidative beer stability show differences of more than 8 h (more than 500%) at a PBN concentration of 50 mM.

In contrast thereto, the EAP determination reflects the non-falsified conditions in the beer in a very high resolution and is characterized by a high reliability of the EAP values.

Example 8

Lag Time Measurement and EAP Determination as a Function of the $SO_2$ Content

The high reliability of the EAP determination can be used to observe and detect in a detailed manner the fundamental radical reactions which are important for oxidative beer stability and the effects of the essential components of oxidative beer stability, namely oxygen and antioxidative ingredients (e.g. $SO_2$, Maillard reaction products, ascorbic acid, metal ions, etc.).

FIG. 10 shows a comparison between the measured lag time (FIG. 10A, B) [13] and the measured EAP value (FIG. 10C, D) as a function of the $SO_2$ content of a beer sample.

The lag time values in FIG. 10A show a non-linear dependence of the $SO_2$ content of a beer sample on the oxidative beer stability. The dependence of the $SO_2$ content, which is confirmed in a number of publications [e.g. 11], can be described to some extent via a saturation curve. The results of the EAP determination (FIG. 10C, D) in principle go against this theory. Instead, the EAP determination shows that in actual fact there is an approximately linear relationship between the $SO_2$ content of a beer sample and the oxidative beer stability.

In order to be able to explain the greatly different results, reference must also be made in this connection to the pH effect caused by the spin trap reagent PBN, which opposes a linear dependence between the measured lag time and the $SO_2$ content of a beer. Although the lag time values rise as the $SO_2$ content of the beer sample rises, the pH effect on the generation of radicals also becomes greater as the lag time values increase (FIGS. 4 to 6, FIG. 8), and the lag time moves further and further away from the conditions that actually exist in the beer.

If the lag time value of 85 min at an $SO_2$ content of 11.5 mg/l is compared with the EAP value of 335 min at an $SO_2$ content of 11.2 mg/l, the significant falsification of the results in the case of the lag time measurement at approx. 4.2 h is more than apparent. FIG. 10B additionally shows a measurement with a very high $SO_2$ content of the beer sample of 53.3 mg/l. The measured lag time value (156 min) served only to approximately estimate the curve of the deviation.

Admittedly, the high $SO_2$ content of 53.3 mg/l can be considered to be unrealistic for German beers. However, it is of particular interest in connection with other beverages which have an EAP, particularly wine. Based on the logically comprehensible linear dependence of the EAP on the $SO_2$ content of a beverage, deviations of up to 1000% can be predicted for such beverages. This means that, contrary to the general opinion, the lag time values measured e.g. for wine are unsuitable for demonstrating the actual EAP.

Further EAP determinations have also shown that different beers with the same $SO_2$ content have different EAP values. This can be justified by the fact that, apart from the significant and linear dependence of the EAP values on the $SO_2$ content, other beer ingredients (metal ions in their effect via the Fenton and Haber-Weiss reaction, Maillard reaction products, phenolic ingredients, etc.) are involved in the oxidative beer stability. Furthermore, the rate of radical generation is influenced by the original initial pH of the beverage sample (see FIG. 2).

Example 9

EAP Determination in Juice and Wine

It can be seen from FIGS. 13 to 19 that the EAP determination can also be used to detect the EAP of other beverages (e.g. in juice or wine). Compared to beer, in the juice sector in particular the addition of ascorbic acid (vitamin C) leads to very high EAP values, while the high EAP values in the wine sector (FIG. 18) can largely be attributed to the higher $SO_2$ contents in the wine.

A direct comparison of FIG. 14 and FIG. 15 provides initial indications that, besides ascorbic acid, the other vitamins in a juice (e.g. a multivitamin juice) are also involved in the EAP. This was able to be confirmed by additional measurements using carrot juices, in which in particular pro-vitamin A is responsible for a certain EAP. In other words, in this sector, the EAP determination is designed to demonstrate the effects of certain beverage ingredients on the EAP.

In the case of mixed beer drinks which contain e.g. "Fresh Lemon" lemonade (FIG. 20), the EAP is determined essentially by the $SO_2$ content of the beer and the ascorbic acid content of the "Fresh Lemon" lemonade. Both ingredients lead to correspondingly high EAP values in this mixed beverage.

For juices, an EtOH addition of 0-5% by volume is recommended (preferably 3% by volume). As a result, a higher signal intensity of the "trapped" secondary radicals is achieved and the evaluation is facilitated, without significantly influencing the EAP value. For a direct comparison of different juices, the set parameters (temperature, forcing test, EtOH addition, etc.) must be maintained for all measurements (forcing test 60° C. recommended). In the case of naturally cloudy juices with a very high fruit content, centrifugation of the juice samples is required (5000 rpm, 5 min).

Example 10

Practical Use

The method according to the invention can be used not only to demonstrate the effects of the different ingredients. By means of a new parameter, which can be referred to e.g. as the "Beverage Antioxidant Index" (BAX for short), it is also possible to obtain a better description of the characteristics of different types of beer (Pils, Export, etc.) and other beverages, such as wine or juice for example.

Based on the detected linear dependence of the EAP values on the $SO_2$ content, it is possible by corresponding addition to determine the increase in the EAP value relative to 1 mg $SO_2$ content, in order thus to define the new parameter. This parameter makes it possible to demonstrate the effects of additional factors on the oxidative stability of beer and other beverages (metal ions, pH of the sample, other ingredients with an oxidative effect, etc.) in their entirety. For example, it is possible to demonstrate the characteristics of different types of beer with regard to their antioxidative behavior and the differences between individual beers.

In general, i.e. in these cases and all other beverages, it is recommended to add $SO_2$, e.g. by means of $Na_2SO_3$. The parameter $BAX_{(sp)}$ can then be determined based on the following equation:

$$BAX_{(sp)} = \Delta EAP / \Delta SO_2 \text{ content}_{(sp)} [\text{min·l/mg}]$$

Here, "sp" stands for "spiked", i.e. after the addition, and $\Delta EAP$ is the EAP value after the addition of $SO_2$ minus the measured (endogenous) EAP value in the sample.

For many beers, in which the EAP is defined mainly by the $SO_2$ content, this parameter can be determined to a first approximation by the quotient between the measured (determined) EAP value in the sample and the total content of $SO_2$:

$$BAX = EAP_{(total)} / SO_2 \text{ content}_{(total)} [\text{min·l/mg}]$$

The proven linear dependence of the EAP value on the $SO_2$ content of a beer is pronounced to varying degrees (slope) for different beers. The $BAX_{(sp)}$ values of most beers are between 50 and 25 min/mg $SO_2$ content.

The resulting value makes it possible to obtain the additional factors of the oxidative beer or beverage stability in their entirety. For instance, a beer with a relatively low metal ion concentration, a relatively low pH and a relatively high concentration of antioxidative ingredients will have a relatively high oxidative beer or beverage stability per mg $SO_2$/l (EAP value/$SO_2$ content).

Since the $SO_2$ content of a beer can be increased only in an individually restricted manner by controlling the fermentation process, and in Germany a limit value of 10 mg/l is defined, the aim of corresponding brewing measures should be to increase the above-described parameter in order to achieve a sustainable improvement in the oxidative beer stability.

Furthermore, the method according to the invention makes it possible to demonstrate the effects of the individual intermediate stages of the brewing process on the EAP (e.g. fermentation, storage tank, chemico-physical beer stabilization, filtration stages, bottling).

This is shown in FIG. 11 based on the example of the effects of chemico-physical beer stabilization (protein stabilization by means of silica gel and PVPP stabilization by removing a quantity of polyphenols).

In the lag time measurement (PBN in FIG. 11A), different final concentrations of spin trap adducts can be ascertained but the lag time values as a criterion for the EAP do not show any appreciable differences. By contrast, in the EAP determination (3 mM POBN in FIG. 11B), not only is it possible to see the different final concentrations of spin trap adducts, but at the same time it is possible to detect the effects of individual process stages on the EAP. Without discussing in detail the findings obtained therefrom, the measurements in FIG. 11B clearly show the potential of the EAP determination for this field of application. From a direct comparison of the curves in FIG. 11A and FIG. 11B, it is also possible to see the extent to which the actual EAP (FIG. 11B) in this beer sample is falsified by the addition of PBN (lag time measurement) (approx. 300-350 min→300-350% deviation), and no relationship can be established between the lag time value and the actual EAP.

Another field of application for EAP determination results directly from the effect of the packaging materials on the oxidative beer stability. Particularly in the upper EAP value range, the avoiding of the pH effects leads to a significantly higher resolution of the results. The EAP determination is therefore suitable for demonstrating, with a high level of accuracy, the effects on oxidative beer stability caused by the oxygen permeation through the various packaging materials (e.g. crown caps, crown caps with $O_2$ scavenger properties, types of clip closures, plastic bottles made from PET or PEN, etc). Based on the described properties, it is possible to predict that EAP determination will in future also gain importance in the packaging materials sector.

Last but not least, only a fraction of the previous spin trap concentration (<3.5 mM instead of 50 mM) is required for the EAP determination. As a result, the not inconsiderable costs in the area of spin trap reagents can be reduced by 80%. This corresponds to a cost reduction of 12,000-15,000 Euro per year and brewery (in the case of routine use: approx. 40 measurements/week; cost reduction/measurement approx. 7 Euro; approx. 50 weeks/year; saving 12,000-15,000 Euro/year).

For the breweries, which will in future make routine use of EAP determination, the greater reliability of the EAP values not only provides the possibility of detecting inconsistencies in the brewing process in good time and then of taking appropriate action, but additionally provides an appreciable cost reduction with regard to quality control and quality assurance.

LIST OF REFERENCES

1. UCHIDA, M.; ONO, M: Improvement for Oxidative Flavor Stability of Beer—Role of OH-Radical in Beer Oxidation, J. Am. Soc. Brew. Chem. 54, 4, 198-204, 1996
2. UCHIDA, M.; SUGA, S.; ONO, M.: Improvement for Oxidative Flavor stability of Beer—Rapid Prediction Method for Beer Flavor Stability by Electron Spin Resonance Spectroscopy, J. Am. Soc. Brew. Chem. 54, 4, 205-211, 1996
3. STASKO, A.; RAPTA, P.; MALIK, F.: Charakterisierung der Bierstabilität mit Hilfe von Radikalfängern (eine EPR-studie), Monatsschrift für Brauwissenschaft, 53, 1/2, 4-7, 2000
4. FORSTER, C; SCHWEIGER, J.; NARZISS, L.; BACK, W.; UCHIDA, M.; ONO, M.; YANAGI, K.: Untersuchungen zur Geschmacksstabilität von Bier mittels Elektronenspinresonanz-Spektroskopie freier Radikale, Monatsschrift für Brauwissenschaft, 52, 5/6, 86-93, 1999
5. FORSTER, C: Die antioxidative Aktivität von Bier—eine neue Methode zur Verbesserung der Geschmacksstabilität, Mitteilungen österreichisches Getränkeinstitut, 11/12, 132-139, 1998
6. YANAGI, K.; ISHIBASHI, Y.; OKA, K.; UCHIDA, M.: Neue Methoden zur Beurteilung von Geschmacksstabilität, Schaumeigenschaften und -stabilität von Bier, Brauwelt, 21/22, 841-859, 1997
7. ANDERSEN, M. L.; OUTTRUP, H.; SKIBSTED, H.: Potential Antioxidants in Beer Assessed by ESR Spin Trapping, J. Agr. Food Chem. 48, 8, 3106-3111, 2000
8. KANEDA, H.; OSAWA, T.; KAWAKISHI, S.; MUNEKATA, M.; KOSHINO, S.: Contribution of carbonyl-bisulfite adducts to beer stability, J. Agr. Food Chem. 42, 2428-2432, 1994
9. KANEDA, H.; MASACHIKA, T.; OSAWA, T.; KAWAKISHI, S.; TAMAKI, T.: Behavior of Sulfites during Fermentation and Storage of Beer, J. Am. Soc. Brew. Chem., 54, 2, 115-120, 1996
10. WALTERS, M. T.: Natural antioxidants and flavour stability, Ferment 10, 2, 111-119, 1997

11. UCHIDA, M.; ONO, M.: Technological Approach to Improve Beer Flavor Stability: Analysis of the Effect of Brewing Processes on Beer Flavor Stability by the Electron Spin Resonance Method, J. Am. Soc. Brew. Chem. 58, 1, 8-13, 2000
12. KANEDA, H.; KANO, Y; OSAWA, T.; RAMARATHNAM, N.; KAWAKISHI, S.; KAMADA, K.: Detection of Free Radicals in Beer Oxidation, Journal of Food Science, 53, 885-888, 1988
13. KUNZ, T.; STEPHAN, A.; METHNER, F. J.; KAPPL, R.; HÜTTERMANN, J.: Grundlegendes zur Elektronenspinresonanz-Spektroskopie (ESR) und Untersuchungen zum Zusammenhang zwischen oxidativer Bierstabilität und dem $SO_2$-Gehalt, Monatsschrift für Brauwissenschaft 55, No 7/8, 140-153, 2002
14. WACKERBAUER, K.; HARDT, R.: Radikalreaktionen und die Geschmacksstabilität des Bieres, Brauwelt, 40/41, 1880-1888, 1996
15. BACK, W.; FORSTER, C; KROTTENTHALER, M.; LEHMANN, J.; SACHER, B.; THUN, B.: Neue Forschungserkenntnisse zur Verbesserung der Geschmacksstabilität, Brauwelt, 38, 1677-1692, 1997
16. KUNZ, T.: Untersuchungen zur oxidativen Bierstabilität mittels Elektronenspinresonanz (ESR), Diplomarbeit, FH Trier, 2002
17. ANDERSEN, M. L.; SKIBSTED, L. H.: Electron Spin Resonance Spin Trapping Identification of Radicals Formed during Aerobic Forced Aging of Beer, J. Agr. Food Chem., 46, 1272-1275, 1998
18. KUNZ, T.; KAPPL, R.; METHNER, F. J.; STEPHAN, A.; HÜTTERMANN, J.: Einfluss physiko-chemischer Parameter auf die Lag-Time Messung, currently being prepared
19. BISHOP, D.; STERN, G.; FLEISCHMANN, M.; MARSHALL, L.: Hydrogen Peroxide Catalytic Oxidation of Refractory Organics in Municipal Waste Water, I&EC Process Design and Development, 7, 110-117, 1968
20. MILLERO, F. J.; SOTOLONGO, S.; STADE, D. J.; VEGA, C. A.: Effect of Ionic Interactions on the Oxidation of Fe (II) with $H_2O_2$ in Aqueous Solutions, Journal of Solution Chemistry, Vol. 20, No. 11, 1079-1092, 1991
21. STEPHAN, A.; BIES, A; KUNZ, T.; METHNER, F. J.: Determination of antioxidants in brewing: Some aspects about the use of selected chemical and physical assays, European Brewery Convention, Monograph 31, Symposium Flavour and Flavour Stability, Nancy/France 2001, Fachverlag Hans Karl, Nürnberg
22. FRANZ, O.; BACK, W.: Erfahrungen zur Messung von freien Radikalen mittels Elektronenresonanz-Spektrometer in der Brauerei, Monatsschrift für Brauwissenschaft 55, No 7/8, 156-162, 2002
23. POU, S.; RAMOS C. L.; GLADWELL, T.; RENKS, E.; CENTRA, M.; YOUNG, D.; COHEN, M. S.; ROSEN, G. M. A Kinetic Approach to the Selection of a Sensitive Spin Trapping System for the Detection of Hydroxyl Radical, Analytical biochemistry 217, 76-83, 1994

The invention claimed is:

1. A method for determining an endogenous antioxidative potential in a sample, comprising
   (a) providing the sample, wherein the sample is a beverage sample selected from the group consisting of a sample of beer, wine, Juice and mixtures thereof;
   (b) adding a spin trap reagent to the sample, wherein the spin trap reagent is POBN, such that the concentration of the spin trap reagent in the sample is $\leq 5$ mM;
   (c) carrying out qualitative and/or quantitative analysis of a secondary radical, which is stabilized by the spin trap reagent, using ESR spectroscopy, wherein the spin trap reagent is suitable for making it possible to avoid the pH effect and the associated influence on the generation of radicals in the sample; and
   (d) determining the EAP value.

2. The method according to claim 1, wherein the sample is a beer sample.

3. The method according to claim 1, wherein the concentration of the spin trap reagent in the sample is 3 mM.

4. The method according to claim 1, wherein the spin trap reagent is soluble in the sample and is dissolved in the sample.

5. The method according to claim 1, wherein the step of adding a spin trap reagent comprises dissolving the spin trap reagent in an aqueous ethanol solution or another aqueous solution and then adding the spin trap reagent aqueous solution to the sample.

6. The method according to claim 1, wherein the secondary radical is a hydroxyethyl radical.

7. The method according to claim 1, wherein the step of carrying-out the analysis in step (c) comprises carrying out a forcing test.

8. The method according to claim 7, wherein the forcing test is carried out at a temperature in the range from $\geq 40°$ C. to $\leq 96°$ C.

9. The method according to claim 7, wherein the forcing test is carried out at a temperature in the range from $\geq 60°$ C. to $\leq 96°$ C.

10. The method according to claim 7, wherein the forcing test is carried out at a temperature in the range from 63-65° C. with beer as the sample, 65-70° C. with wine as the sample, and 60° C. with juice as the sample.

11. The method according to claim 7, wherein the forcing test is carried out at a temperature of 63° C.

12. The method according to claim 7, wherein the forcing test is carried out at a pH which lies in a range extending from one pH point below to one pH point above the pH of the sample.

13. The method according to claim 7, wherein the forcing test is carried out at a pH which lies in a range extending from 0.5 pH point below to 0.5 pH point above the pH of the sample.

14. The method according to claim 7, wherein the forcing test is carried out at a pH which corresponds to the pH of the sample.

15. The method according to claim 7, wherein the forcing test is carried out in the presence of ethanol in a concentration in the range from 0.01-20% by volume.

16. The method according to claim 7, wherein the forcing test is carried out in the presence of ethanol in a concentration in the range from 0.01-10% by volume.

17. The method according to claim 7, wherein the forcing test is carried out in the presence of ethanol in a concentration in the range from 0.01-6.0% by volume.

18. The method according to claim 7, wherein the forcing test is carried out in the presence of ethanol in a concentration in the range from 0.01-3.0% by volume.

19. The method according to claim 1, wherein the step of carrying-out of analysis in step (c) comprises the following sub-steps:
   (c1) taking a measurement sample at a given time; and
   (c2) recording the ESR spectrum of the measurement sample.

20. The method according to claim 19, wherein the time period between sub-steps (c1) and (c2) is $\leq 15$ min.

21. The method according to claim 19, wherein the time period between sub-steps (c1) and (c2) is 4 min.

22. The method according to claim 1, wherein the method comprises a system which promotes the generation of radicals.

23. The method according to claim 1, further comprising carrying out qualitative and/or quantitative analysis of the effect of an oxidatively neutral, antioxidative or oxidative compound selected from the group consisting of oxygen, $SO_2$, Maillard reaction products, ascorbic acid and other Vitamins, metal ions, phenolic compounds, organic acids, proteins, polypeptides, amino acids, alcohols, and salts.

24. The method according to claim 23, wherein the antioxidative compound is $SO_2$.

25. The method according to claim 23, wherein the antioxidative compound is ascorbic acid.

26. The method according to claim 23, wherein the oxidative compound is oxygen.

27. The method according to claim 23, wherein the phenol carboxylic acid is gallic acid.

28. The method according to claim 1, further comprising adding $SO_2$ to the sample, and determining a quotient $BAX_{(sp)}$ of the rise in the endogenous antioxidative potential EAP in the sample and the content of $SO_2$ in the sample according to the following formula:

$$BAX_{(sp)} = \Delta EAP / \Delta SO_2 \text{ content}_{(sp)} [\min \cdot 1/mg]$$

in which $\Delta$ EAP is the EAP value after the addition of $SO_2$ minus the EAP value before the addition of $SO_2$, and in which $\Delta SO_2$ content is the $SO_2$ content brought about as a result of the addition.

29. The method according to claim 1, further comprising determining a quotient BAX of the total endogenous antioxidative potential EAP in the sample and the total content of $SO_2$ in the sample according to the following formula:

$$BAX = EAP_{(total)} / SO_2 \text{ content}_{(total)} [\min \cdot 1/mg].$$

* * * * *